US009390229B1

(12) United States Patent
Kahn et al.

(10) Patent No.: US 9,390,229 B1
(45) Date of Patent: Jul. 12, 2016

(54) METHOD AND APPARATUS FOR A HEALTH PHONE

(75) Inventors: Philippe Richard Kahn, Santa Cruz, CA (US); Arthur Kinsolving, Santa Cruz, CA (US)

(73) Assignee: DP TECHNOLOGIES, INC., Scotts Valley, CA (US)

(*) Notice: Subject to any disclaimer, the term of this patent is extended or adjusted under 35 U.S.C. 154(b) by 80 days.

(21) Appl. No.: 11/740,884

(22) Filed: Apr. 26, 2007

Related U.S. Application Data

(60) Provisional application No. 60/795,398, filed on Apr. 26, 2006.

(51) Int. Cl.
*A61B 5/00* (2006.01)
*G06F 19/00* (2011.01)
*A63B 22/02* (2006.01)
*A63B 22/04* (2006.01)

(52) U.S. Cl.
CPC ............ *G06F 19/34* (2013.01); *G06F 19/3456* (2013.01); *A63B 22/02* (2013.01); *A63B 22/04* (2013.01)

(58) Field of Classification Search
CPC .... A63B 22/02; A63B 22/04; A63B 23/0458; A63B 2022/0069; G06F 19/34; G06F 19/3456; G06F 19/3475–19/3481
USPC .............................................. 600/300; 4/300
See application file for complete search history.

(56) References Cited

U.S. PATENT DOCUMENTS

| | | | |
|---|---|---|---|
| 4,285,041 A | 8/1981 | Smith | |
| 4,571,680 A | 2/1986 | Wu | |
| 4,578,769 A | 3/1986 | Frederick | |
| 4,700,369 A | 10/1987 | Siegal et al. | |
| 4,776,323 A | 10/1988 | Spector | |
| 5,313,060 A | 5/1994 | Gast et al. | |
| 5,386,210 A | 1/1995 | Lee | |
| 5,430,480 A | 7/1995 | Allen et al. | |
| 5,446,725 A | 8/1995 | Ishiwatari | |
| 5,446,775 A | 8/1995 | Wright et al. | |

(Continued)

FOREIGN PATENT DOCUMENTS

| | | |
|---|---|---|
| EP | 1 104 143 | 5/2001 |
| EP | 0 833 537 | 7/2002 |

(Continued)

OTHER PUBLICATIONS

"Access and Terminals (AT); Multimedia Message Service (MMS) for PSTN/ISDN; Multimedia Message Communication Between a Fixed Network Multimedia Message Terminal Equipment and a Multimedia Message Service Centre," ETSI AT-F Rapporteur Meeting, Feb. 4-6, 2003, Gothenburg, DES/AT-030023 V0.0.1 (Mar. 2003).

(Continued)

*Primary Examiner* — Gary Jackson
*Assistant Examiner* — Shirley Jian
(74) *Attorney, Agent, or Firm* — HIPLegal LLP; Judith Szepesi

(57) ABSTRACT

A method and apparatus providing a health phone utilizing a pedometer or accelerometer incorporated into a cellular telephone. The system is designed to receive activity data from the pedometer or accelerometer, and communicate the activity data to a remote server, the cellular telephone further designed to receive suggestions from the server, the suggestions generated based on the activity data received from the cellular telephone.

20 Claims, 15 Drawing Sheets

(56) References Cited

U.S. PATENT DOCUMENTS

| | | | |
|---|---|---|---|
| 5,454,114 A | 9/1995 | Yach et al. | |
| 5,485,402 A | 1/1996 | Smith et al. | |
| 5,506,987 A | 4/1996 | Abramson et al. | |
| 5,515,419 A | 5/1996 | Sheffer | |
| 5,583,776 A | 12/1996 | Levi et al. | |
| 5,593,431 A | 1/1997 | Sheldon | |
| 5,654,619 A | 8/1997 | Iwashita | |
| 5,703,786 A * | 12/1997 | Conkright | 700/244 |
| 5,737,439 A | 4/1998 | Lapsley et al. | |
| 5,771,001 A | 6/1998 | Cobb | |
| 5,778,882 A | 7/1998 | Raymond et al. | |
| 5,911,065 A | 6/1999 | Williams et al. | |
| 5,955,667 A | 9/1999 | Fyfe | |
| 5,955,871 A * | 9/1999 | Nguyen | 323/282 |
| 5,960,085 A | 9/1999 | de la Huerga | |
| 5,976,083 A | 11/1999 | Richardson et al. | |
| 6,013,007 A * | 1/2000 | Root et al. | 482/8 |
| 6,061,456 A | 5/2000 | Andrea et al. | |
| 6,122,595 A | 9/2000 | Varley et al. | |
| 6,135,951 A | 10/2000 | Richardson et al. | |
| 6,145,389 A | 11/2000 | Ebeling et al. | |
| 6,246,321 B1 | 6/2001 | Rechsteiner et al. | |
| 6,282,496 B1 | 8/2001 | Chowdhary | |
| 6,336,891 B1 * | 1/2002 | Fedrigon et al. | 482/8 |
| 6,353,449 B1 | 3/2002 | Gregg et al. | |
| 6,369,794 B1 | 4/2002 | Sakurai et al. | |
| 6,396,883 B2 | 5/2002 | Yang et al. | |
| 6,408,330 B1 | 6/2002 | de la Huerga | |
| 6,428,490 B1 | 8/2002 | Kramer et al. | |
| 6,470,147 B1 | 10/2002 | Imada | |
| 6,478,736 B1 * | 11/2002 | Mault | 600/300 |
| 6,493,652 B1 | 12/2002 | Ohlenbusch et al. | |
| 6,496,695 B1 | 12/2002 | Kouji et al. | |
| 6,513,381 B2 | 2/2003 | Fyfe et al. | |
| 6,522,266 B1 | 2/2003 | Soehren et al. | |
| 6,529,144 B1 | 3/2003 | Nilsen et al. | |
| 6,532,419 B1 | 3/2003 | Begin et al. | |
| 6,539,336 B1 | 3/2003 | Vock et al. | |
| 6,595,929 B2 * | 7/2003 | Stivoric et al. | 600/549 |
| 6,601,016 B1 * | 7/2003 | Brown et al. | 702/182 |
| 6,607,493 B2 | 8/2003 | Song | |
| 6,611,789 B1 | 8/2003 | Darley | |
| 6,628,898 B2 | 9/2003 | Endo | |
| 6,634,992 B1 * | 10/2003 | Ogawa | 482/8 |
| 6,665,802 B1 | 12/2003 | Ober | |
| 6,672,991 B2 | 1/2004 | O'Malley | |
| 6,685,480 B2 | 2/2004 | Nishimoto et al. | |
| 6,700,499 B2 | 3/2004 | Kubo et al. | |
| 6,731,958 B1 | 5/2004 | Shirai | |
| 6,766,176 B1 | 7/2004 | Gupta et al. | |
| 6,771,250 B1 | 8/2004 | Oh | |
| 6,786,877 B2 | 9/2004 | Foxlin | |
| 6,788,980 B1 | 9/2004 | Johnson | |
| 6,790,178 B1 * | 9/2004 | Mault et al. | 600/300 |
| 6,813,582 B2 | 11/2004 | Levi et al. | |
| 6,823,036 B1 | 11/2004 | Chen | |
| 6,826,477 B2 | 11/2004 | Ladetto et al. | |
| 6,836,744 B1 | 12/2004 | Asphahani et al. | |
| 6,881,191 B2 | 4/2005 | Oakley et al. | |
| 6,885,971 B2 | 4/2005 | Vock et al. | |
| 6,895,425 B1 | 5/2005 | Kadyk et al. | |
| 6,898,550 B1 | 5/2005 | Blackadar et al. | |
| 6,928,382 B2 | 8/2005 | Hong et al. | |
| 6,941,239 B2 | 9/2005 | Unuma et al. | |
| 6,959,259 B2 | 10/2005 | Vock et al. | |
| 6,975,959 B2 | 12/2005 | Dietrich et al. | |
| 6,997,852 B2 * | 2/2006 | Watterson et al. | 482/1 |
| 7,002,553 B2 | 2/2006 | Shkolnikov | |
| 7,010,332 B1 | 3/2006 | Irvin et al. | |
| 7,020,487 B2 | 3/2006 | Kimata | |
| 7,027,087 B2 | 4/2006 | Nozaki et al. | |
| 7,028,547 B2 | 4/2006 | Shiratori et al. | |
| 7,042,509 B2 | 5/2006 | Onuki | |
| 7,054,784 B2 | 5/2006 | Flentov et al. | |
| 7,057,551 B1 | 6/2006 | Vogt | |
| 7,072,789 B2 | 7/2006 | Vock et al. | |
| 7,092,846 B2 | 8/2006 | Vock et al. | |
| 7,096,619 B2 | 8/2006 | Jackson et al. | |
| 7,148,797 B2 | 12/2006 | Albert | |
| 7,148,879 B2 | 12/2006 | Amento et al. | |
| 7,149,964 B1 | 12/2006 | Cottrille et al. | |
| 7,155,507 B2 | 12/2006 | Hirano et al. | |
| 7,158,912 B2 | 1/2007 | Vock et al. | |
| 7,169,084 B2 | 1/2007 | Tsuji | |
| 7,171,222 B2 | 1/2007 | Fostick | |
| 7,171,331 B2 | 1/2007 | Vock et al. | |
| 7,173,604 B2 | 2/2007 | Marvit et al. | |
| 7,176,886 B2 | 2/2007 | Marvit et al. | |
| 7,176,887 B2 | 2/2007 | Marvit et al. | |
| 7,176,888 B2 | 2/2007 | Marvit et al. | |
| 7,177,684 B1 | 2/2007 | Kroll et al. | |
| 7,180,500 B2 | 2/2007 | Marvit et al. | |
| 7,180,501 B2 | 2/2007 | Marvit et al. | |
| 7,180,502 B2 | 2/2007 | Marvit et al. | |
| 7,200,517 B2 | 4/2007 | Darley et al. | |
| 7,212,230 B2 | 5/2007 | Stavely | |
| 7,212,943 B2 | 5/2007 | Aoshima et al. | |
| 7,220,220 B2 | 5/2007 | Stubbs et al. | |
| 7,245,725 B1 | 7/2007 | Beard | |
| 7,254,516 B2 * | 8/2007 | Case et al. | 702/182 |
| 7,280,096 B2 | 10/2007 | Marvit et al. | |
| 7,280,849 B1 | 10/2007 | Bailey | |
| 7,297,088 B2 | 11/2007 | Tsuji | |
| 7,301,526 B2 | 11/2007 | Marvit et al. | |
| 7,301,527 B2 | 11/2007 | Marvit et al. | |
| 7,301,528 B2 | 11/2007 | Marvit et al. | |
| 7,301,529 B2 | 11/2007 | Marvit et al. | |
| 7,305,323 B2 | 12/2007 | Skvortsov et al. | |
| 7,328,611 B2 | 2/2008 | Klees et al. | |
| 7,334,472 B2 | 2/2008 | Seo et al. | |
| 7,353,112 B2 | 4/2008 | Choi et al. | |
| 7,365,735 B2 | 4/2008 | Reinhardt et al. | |
| 7,365,736 B2 | 4/2008 | Marvit et al. | |
| 7,365,737 B2 | 4/2008 | Marvit et al. | |
| 7,379,999 B1 | 5/2008 | Zhou et al. | |
| 7,387,611 B2 | 6/2008 | Inoue et al. | |
| 7,397,357 B2 | 7/2008 | Krumm et al. | |
| 7,451,056 B2 | 11/2008 | Flentov et al. | |
| 7,457,719 B1 | 11/2008 | Kahn et al. | |
| 7,457,872 B2 | 11/2008 | Aton et al. | |
| 7,463,997 B2 | 12/2008 | Pasolini et al. | |
| 7,467,060 B2 | 12/2008 | Kulach et al. | |
| 7,502,643 B2 * | 3/2009 | Farringdon et al. | 600/509 |
| 7,512,515 B2 | 3/2009 | Vock et al. | |
| 7,526,402 B2 | 4/2009 | Tenenhaus et al. | |
| 7,608,050 B2 | 10/2009 | Sugg | |
| 7,640,804 B2 | 1/2010 | Daumer et al. | |
| 7,647,196 B2 | 1/2010 | Kahn et al. | |
| 7,653,508 B1 | 1/2010 | Kahn et al. | |
| 7,664,657 B1 | 2/2010 | Letzt et al. | |
| 7,689,107 B2 | 3/2010 | Enomoto | |
| 7,705,884 B2 | 4/2010 | Pinto et al. | |
| 7,736,272 B2 * | 6/2010 | Martens | 482/8 |
| 7,752,011 B2 | 7/2010 | Niva et al. | |
| 7,753,861 B1 | 7/2010 | Kahn et al. | |
| 7,765,553 B2 | 7/2010 | Douceur et al. | |
| 7,774,156 B2 | 8/2010 | Niva et al. | |
| 7,788,059 B1 | 8/2010 | Kahn et al. | |
| 7,840,346 B2 * | 11/2010 | Huhtala et al. | 701/439 |
| 7,857,772 B2 | 12/2010 | Bouvier et al. | |
| 7,881,902 B1 | 2/2011 | Kahn et al. | |
| 7,892,080 B1 | 2/2011 | Dahl | |
| 7,987,070 B2 | 7/2011 | Kahn et al. | |
| 8,187,182 B2 | 5/2012 | Kahn et al. | |
| 8,275,635 B2 * | 9/2012 | Stivoric et al. | 705/3 |
| 8,398,546 B2 * | 3/2013 | Pacione et al. | 600/300 |
| 8,562,489 B2 * | 10/2013 | Burton et al. | 482/9 |
| 8,790,279 B2 * | 7/2014 | Brunner | 600/595 |
| 2001/0047488 A1 | 11/2001 | Verplaetse et al. | |
| 2002/0006284 A1 | 1/2002 | Kim | |
| 2002/0022551 A1 * | 2/2002 | Watterson et al. | 482/8 |
| 2002/0023654 A1 | 2/2002 | Webb | |
| 2002/0027164 A1 * | 3/2002 | Mault et al. | 235/462.46 |
| 2002/0042830 A1 | 4/2002 | Bose et al. | |

(56) References Cited

U.S. PATENT DOCUMENTS

| | | |
|---|---|---|
| 2002/0044634 A1 | 4/2002 | Rooke et al. |
| 2002/0054214 A1 | 5/2002 | Yoshikawa |
| 2002/0089425 A1 | 7/2002 | Kubo et al. |
| 2002/0109600 A1* | 8/2002 | Mault et al. ............. 340/573.1 |
| 2002/0118121 A1 | 8/2002 | Lehrman et al. |
| 2002/0122543 A1 | 9/2002 | Rowen |
| 2002/0138017 A1 | 9/2002 | Bui et al. |
| 2002/0142887 A1 | 10/2002 | O'Malley |
| 2002/0150302 A1 | 10/2002 | McCarthy et al. |
| 2002/0151810 A1 | 10/2002 | Wong et al. |
| 2002/0173295 A1 | 11/2002 | Nykanen et al. |
| 2002/0190947 A1 | 12/2002 | Feinstein |
| 2003/0018430 A1 | 1/2003 | Ladetto et al. |
| 2003/0033411 A1 | 2/2003 | Kavoori et al. |
| 2003/0048218 A1 | 3/2003 | Milnes et al. |
| 2003/0083596 A1 | 5/2003 | Kramer et al. |
| 2003/0093187 A1 | 5/2003 | Walker et al. |
| 2003/0101260 A1 | 5/2003 | Dacier et al. |
| 2003/0109258 A1 | 6/2003 | Mantyjarvi et al. |
| 2003/0139692 A1 | 7/2003 | Barrey et al. |
| 2003/0139908 A1 | 7/2003 | Wegerich et al. |
| 2003/0149526 A1 | 8/2003 | Zhou et al. |
| 2003/0151672 A1 | 8/2003 | Robins et al. |
| 2003/0187683 A1* | 10/2003 | Kirchhoff et al. .............. 705/1 |
| 2003/0208110 A1* | 11/2003 | Mault et al. ................ 600/300 |
| 2003/0208113 A1* | 11/2003 | Mault et al. ................ 600/316 |
| 2003/0227487 A1 | 12/2003 | Hugh |
| 2003/0236625 A1 | 12/2003 | Brown et al. |
| 2004/0017300 A1 | 1/2004 | Kotzin et al. |
| 2004/0024846 A1 | 2/2004 | Randall et al. |
| 2004/0043760 A1 | 3/2004 | Rosenfeld et al. |
| 2004/0044493 A1 | 3/2004 | Coulthard |
| 2004/0047498 A1 | 3/2004 | Mulet-Parada et al. |
| 2004/0078219 A1 | 4/2004 | Kaylor et al. |
| 2004/0078220 A1 | 4/2004 | Jackson |
| 2004/0081441 A1 | 4/2004 | Sato et al. |
| 2004/0106958 A1 | 6/2004 | Mathis et al. |
| 2004/0122294 A1 | 6/2004 | Hatlestad et al. |
| 2004/0122295 A1 | 6/2004 | Hatlestad et al. |
| 2004/0122296 A1 | 6/2004 | Hatlestad et al. |
| 2004/0122297 A1 | 6/2004 | Stahmann et al. |
| 2004/0122333 A1 | 6/2004 | Nissila |
| 2004/0122484 A1 | 6/2004 | Hatlestad et al. |
| 2004/0122485 A1 | 6/2004 | Stahmann et al. |
| 2004/0122486 A1 | 6/2004 | Stahmann et al. |
| 2004/0122487 A1 | 6/2004 | Hatlestad et al. |
| 2004/0125073 A1 | 7/2004 | Potter et al. |
| 2004/0130628 A1 | 7/2004 | Stavely |
| 2004/0135898 A1 | 7/2004 | Zador |
| 2004/0146048 A1 | 7/2004 | Cotte |
| 2004/0148340 A1 | 7/2004 | Cotte |
| 2004/0148341 A1 | 7/2004 | Cotte |
| 2004/0148342 A1 | 7/2004 | Cotte |
| 2004/0148351 A1 | 7/2004 | Cotte |
| 2004/0176067 A1 | 9/2004 | Lakhani et al. |
| 2004/0185821 A1 | 9/2004 | Yuasa |
| 2004/0219910 A1* | 11/2004 | Beckers ................ 455/422.1 |
| 2004/0225467 A1 | 11/2004 | Vock et al. |
| 2004/0236500 A1 | 11/2004 | Choi et al. |
| 2004/0242202 A1 | 12/2004 | Torvinen |
| 2004/0247030 A1 | 12/2004 | Wiethoff |
| 2004/0259494 A1 | 12/2004 | Mazar |
| 2005/0015768 A1 | 1/2005 | Moore |
| 2005/0027567 A1 | 2/2005 | Taha |
| 2005/0033200 A1 | 2/2005 | Soehren et al. |
| 2005/0038691 A1 | 2/2005 | Babu |
| 2005/0048945 A1 | 3/2005 | Porter |
| 2005/0048955 A1 | 3/2005 | Ring |
| 2005/0078197 A1 | 4/2005 | Gonzales |
| 2005/0079873 A1 | 4/2005 | Caspi et al. |
| 2005/0101841 A9 | 5/2005 | Kaylor et al. |
| 2005/0102167 A1 | 5/2005 | Kapoor |
| 2005/0107944 A1 | 5/2005 | Hovestadt et al. |
| 2005/0113649 A1* | 5/2005 | Bergantino ................ 600/300 |
| 2005/0113650 A1 | 5/2005 | Pacione et al. |
| 2005/0131736 A1 | 6/2005 | Nelson et al. |
| 2005/0141522 A1 | 6/2005 | Kadar et al. |
| 2005/0143106 A1 | 6/2005 | Chan et al. |
| 2005/0146431 A1 | 7/2005 | Hastings et al. |
| 2005/0157181 A1 | 7/2005 | Kawahara et al. |
| 2005/0165719 A1 | 7/2005 | Greenspan et al. |
| 2005/0168587 A1 | 8/2005 | Sato et al. |
| 2005/0182824 A1 | 8/2005 | Cotte |
| 2005/0183086 A1 | 8/2005 | Abe et al. |
| 2005/0202934 A1 | 9/2005 | Olrik et al. |
| 2005/0203430 A1 | 9/2005 | Williams et al. |
| 2005/0210300 A1* | 9/2005 | Song et al. ................ 713/300 |
| 2005/0212751 A1 | 9/2005 | Marvit et al. |
| 2005/0212752 A1 | 9/2005 | Marvit et al. |
| 2005/0212753 A1 | 9/2005 | Marvit et al. |
| 2005/0212760 A1 | 9/2005 | Marvit et al. |
| 2005/0216403 A1 | 9/2005 | Tam et al. |
| 2005/0222801 A1 | 10/2005 | Wulff et al. |
| 2005/0232388 A1 | 10/2005 | Tsuji |
| 2005/0232404 A1 | 10/2005 | Gaskill |
| 2005/0234676 A1 | 10/2005 | Shibayama |
| 2005/0235058 A1 | 10/2005 | Rackus et al. |
| 2005/0238132 A1 | 10/2005 | Tsuji |
| 2005/0240375 A1 | 10/2005 | Sugai |
| 2005/0243178 A1 | 11/2005 | McConica |
| 2005/0245988 A1 | 11/2005 | Miesel |
| 2005/0248718 A1 | 11/2005 | Howell et al. |
| 2005/0256414 A1 | 11/2005 | Kettunen et al. |
| 2005/0258938 A1 | 11/2005 | Moulson |
| 2005/0262237 A1 | 11/2005 | Fulton et al. |
| 2005/0281289 A1 | 12/2005 | Huang et al. |
| 2006/0009243 A1 | 1/2006 | Dahan et al. |
| 2006/0017692 A1 | 1/2006 | Wehrenberg et al. |
| 2006/0020177 A1 | 1/2006 | Seo et al. |
| 2006/0029284 A1 | 2/2006 | Stewart |
| 2006/0040793 A1* | 2/2006 | Martens ......................... 482/8 |
| 2006/0063980 A1 | 3/2006 | Hwang et al. |
| 2006/0064276 A1 | 3/2006 | Ren et al. |
| 2006/0080551 A1 | 4/2006 | Mantyjarvi et al. |
| 2006/0090088 A1 | 4/2006 | Choi et al. |
| 2006/0090161 A1 | 4/2006 | Bodas et al. |
| 2006/0098097 A1 | 5/2006 | Wach et al. |
| 2006/0100546 A1 | 5/2006 | Silk |
| 2006/0109113 A1 | 5/2006 | Reyes et al. |
| 2006/0136173 A1* | 6/2006 | Case et al. ................ 702/182 |
| 2006/0140422 A1 | 6/2006 | Zurek et al. |
| 2006/0149516 A1 | 7/2006 | Bond et al. |
| 2006/0154642 A1 | 7/2006 | Scannell, Jr. |
| 2006/0161377 A1 | 7/2006 | Rakkola et al. |
| 2006/0161459 A9 | 7/2006 | Rosenfeld et al. |
| 2006/0167387 A1 | 7/2006 | Buchholz et al. |
| 2006/0167647 A1 | 7/2006 | Krumm et al. |
| 2006/0167943 A1 | 7/2006 | Rosenberg |
| 2006/0172706 A1 | 8/2006 | Griffin et al. |
| 2006/0174685 A1 | 8/2006 | Skvortsov et al. |
| 2006/0201964 A1 | 9/2006 | DiPerna et al. |
| 2006/0204214 A1 | 9/2006 | Shah et al. |
| 2006/0206258 A1 | 9/2006 | Brooks |
| 2006/0223547 A1 | 10/2006 | Chin et al. |
| 2006/0249683 A1 | 11/2006 | Goldberg et al. |
| 2006/0256082 A1 | 11/2006 | Cho et al. |
| 2006/0257042 A1 | 11/2006 | Ofek et al. |
| 2006/0259268 A1 | 11/2006 | Vock et al. |
| 2006/0284979 A1 | 12/2006 | Clarkson |
| 2006/0288781 A1 | 12/2006 | Daumer et al. |
| 2006/0289819 A1 | 12/2006 | Parsons et al. |
| 2007/0004451 A1 | 1/2007 | Anderson |
| 2007/0005988 A1 | 1/2007 | Zhang et al. |
| 2007/0017136 A1 | 1/2007 | Mosher et al. |
| 2007/0024441 A1 | 2/2007 | Kahn et al. |
| 2007/0037605 A1 | 2/2007 | Logan et al. |
| 2007/0038364 A1 | 2/2007 | Lee et al. |
| 2007/0040892 A1 | 2/2007 | Aoki et al. |
| 2007/0050157 A1 | 3/2007 | Kahn et al. |
| 2007/0061105 A1 | 3/2007 | Darley et al. |
| 2007/0063850 A1 | 3/2007 | Devaul et al. |
| 2007/0067094 A1 | 3/2007 | Park et al. |
| 2007/0073482 A1 | 3/2007 | Churchill et al. |
| 2007/0075127 A1 | 4/2007 | Rosenberg |

(56) References Cited

U.S. PATENT DOCUMENTS

| | | |
|---|---|---|
| 2007/0075965 A1 | 4/2007 | Huppi et al. |
| 2007/0082789 A1 | 4/2007 | Nissila et al. |
| 2007/0104479 A1 | 5/2007 | Machida |
| 2007/0106991 A1 | 5/2007 | Yoo |
| 2007/0125852 A1 | 6/2007 | Rosenberg |
| 2007/0130582 A1 | 6/2007 | Chang et al. |
| 2007/0142715 A1 | 6/2007 | Banet et al. |
| 2007/0143068 A1 | 6/2007 | Pasolini et al. |
| 2007/0145680 A1 | 6/2007 | Rosenberg |
| 2007/0150136 A1 | 6/2007 | Doll et al. |
| 2007/0156364 A1 | 7/2007 | Rothkopf |
| 2007/0161410 A1 | 7/2007 | Huang et al. |
| 2007/0165790 A1 | 7/2007 | Taori |
| 2007/0169126 A1 | 7/2007 | Todoroki et al. |
| 2007/0176898 A1 | 8/2007 | Suh |
| 2007/0192483 A1 | 8/2007 | Rezvani et al. |
| 2007/0208531 A1 | 9/2007 | Darley et al. |
| 2007/0208544 A1 | 9/2007 | Kulach et al. |
| 2007/0213126 A1 | 9/2007 | Deutsch et al. |
| 2007/0233788 A1 | 10/2007 | Bender |
| 2007/0239399 A1 | 10/2007 | Shyenblat et al. |
| 2007/0250261 A1 | 10/2007 | Soehren |
| 2007/0259685 A1 | 11/2007 | Engblom et al. |
| 2007/0259716 A1 | 11/2007 | Mattice et al. |
| 2007/0259717 A1 | 11/2007 | Mattice et al. |
| 2007/0260418 A1 | 11/2007 | Ladetto et al. |
| 2007/0260482 A1 | 11/2007 | Nurmela et al. |
| 2007/0263995 A1 | 11/2007 | Park et al. |
| 2007/0281762 A1 | 12/2007 | Barros et al. |
| 2007/0296696 A1 | 12/2007 | Nurmi |
| 2008/0005738 A1 | 1/2008 | Imai et al. |
| 2008/0030586 A1 | 2/2008 | Helbing et al. |
| 2008/0046888 A1 | 2/2008 | Appaji |
| 2008/0052716 A1 | 2/2008 | Theurer |
| 2008/0072014 A1 | 3/2008 | Krishnan et al. |
| 2008/0082994 A1 | 4/2008 | Ito et al. |
| 2008/0102785 A1 | 5/2008 | Childress et al. |
| 2008/0109158 A1* | 5/2008 | Huhtala et al. ............ 701/208 |
| 2008/0113689 A1 | 5/2008 | Bailey |
| 2008/0114538 A1* | 5/2008 | Lindroos ............ 701/208 |
| 2008/0140338 A1 | 6/2008 | No et al. |
| 2008/0153671 A1 | 6/2008 | Ogg et al. |
| 2008/0165022 A1 | 7/2008 | Herz et al. |
| 2008/0168361 A1 | 7/2008 | Forstall et al. |
| 2008/0171918 A1 | 7/2008 | Teller et al. |
| 2008/0214358 A1 | 9/2008 | Ogg et al. |
| 2008/0231713 A1 | 9/2008 | Florea et al. |
| 2008/0231714 A1 | 9/2008 | Estevez et al. |
| 2008/0232604 A1 | 9/2008 | Dufresne et al. |
| 2008/0243432 A1 | 10/2008 | Kato et al. |
| 2008/0303681 A1 | 12/2008 | Herz et al. |
| 2008/0311929 A1 | 12/2008 | Carro et al. |
| 2009/0017880 A1 | 1/2009 | Moore et al. |
| 2009/0031319 A1 | 1/2009 | Fecioru |
| 2009/0043531 A1 | 2/2009 | Kahn et al. |
| 2009/0047645 A1 | 2/2009 | Dibenedetto et al. |
| 2009/0067826 A1 | 3/2009 | Shinohara et al. |
| 2009/0088204 A1 | 4/2009 | Culbert et al. |
| 2009/0099668 A1 | 4/2009 | Lehman et al. |
| 2009/0124348 A1 | 5/2009 | Yoseloff et al. |
| 2009/0124938 A1* | 5/2009 | Brunner ............ 600/595 |
| 2009/0128448 A1 | 5/2009 | Riechel |
| 2009/0174782 A1 | 7/2009 | Kahn et al. |
| 2009/0213002 A1 | 8/2009 | Rani et al. |
| 2009/0215502 A1 | 8/2009 | Griffin, Jr. |
| 2009/0234614 A1 | 9/2009 | Kahn et al. |
| 2009/0274317 A1 | 11/2009 | Kahn et al. |
| 2009/0296951 A1 | 12/2009 | De Haan |
| 2009/0319221 A1 | 12/2009 | Kahn et al. |
| 2009/0325705 A1 | 12/2009 | Filer et al. |
| 2010/0056872 A1 | 3/2010 | Kahn et al. |
| 2010/0057398 A1 | 3/2010 | Darley et al. |
| 2010/0199189 A1 | 8/2010 | Ben-Aroya et al. |
| 2010/0245131 A1 | 9/2010 | Graumann |
| 2010/0277489 A1 | 11/2010 | Geisner et al. |
| 2010/0283742 A1 | 11/2010 | Lam |
| 2011/0003665 A1* | 1/2011 | Burton et al. ............ 482/9 |

FOREIGN PATENT DOCUMENTS

| | | |
|---|---|---|
| GB | 2431813 A | 5/2007 |
| JP | 7020547 A | 1/1995 |
| JP | 2001-057695 | 2/2001 |
| JP | 2003-143683 | 5/2003 |
| JP | 2005-309691 | 11/2005 |
| JP | 2006-118909 | 5/2006 |
| JP | 2006-239398 | 9/2006 |
| JP | 2007-104670 | 4/2007 |
| JP | 2007-215784 | 8/2007 |
| JP | 2007-226855 | 9/2007 |
| WO | WO 99/22338 | 5/1999 |
| WO | WO 00/63874 | 10/2000 |
| WO | WO 02/088926 | 11/2002 |

OTHER PUBLICATIONS

Anderson, Ian, et al, "Shakra: Tracking and Sharing Daily Activity Levels with Unaugmented Mobile Phones," Mobile Netw Appl, Aug. 3, 2007, pp. 185-199.

Ang, Wei Tech, et al, "Zero Phase Filtering for Active Compensation of Period Physiological Motion," Proc 1st IEEE / RAS-EMBS International Conference on Biomedical Robotics and Biomechatronics, Feb. 20-22, 2006, pp. 182-187.

Aylward, Ryan, et al, "Sensemble: A Wireless, Compact, Multi-User Sensor System for Interactive Dance," International Conference on New Interfaces for Musical Expression (NIME06), Jun. 4-8, 2006, pp. 134-139.

Baca, Arnold, et al, "Rapid Feedback Systems for Elite Sports Training," IEEE Pervasive Computing, Oct.-Dec. 2006, pp. 70-76.

Bakhru, Kesh, "A Seamless Tracking Solution for Indoor and Outdoor Position Location," IEEE 16th International Symposium on Personal, Indoor, and Mobile Radio Communications, 2005, pp. 2029-2033.

Bliley, Kara E, et al, "A Miniaturized Low Power Personal Motion Analysis Logger Utilizing MEMS Accelerometers and Low Power Microcontroller," IEEE EMBS Special Topic Conference on Microtechnologies in Medicine and Biology, May 12-15, 2005, pp. 92-93.

Bourzac, Katherine "Wearable Health Reports," Technology Review, Feb. 28, 2006, <http://www.techreview.com/printer_friendly_article_aspx?id+16431>, Mar. 22, 2007, 3 pages.

Cheng, et al, "Periodic Human Motion Description for Sports Video Databases," Proceedings of the Pattern Recognition, 2004, 8 pages.

Dao, Ricardo, "Inclination Sensing with Thermal Accelerometers", MEMSIC, May 2002, 3 pages.

"Decrease Processor Power Consumption using a CoolRunner CPLD," XILINX XAPP347 (v1.0), May 16, 2001, 9 pages.

Fang, Lei, et al, "Design of a Wireless Assisted Pedestrian Dead Reckoning System—The NavMote Experience," IEEE Transactions on Instrumentation and Measurement, vol. 54, No. 6, Dec. 2005, pp. 2342-2358.

Healey, Jennifer, et al, "Wearable Wellness Monitoring Using ECG and Accelerometer Data," IEEE Int. Symposium on Wearable Computers (ISWC'05), 2005, 2 pages.

Hemmes, Jeffrey, et al, "Lessons Learned Building TeamTrak: An Urban/Outdoor Mobile Testbed," 2007 IEEE Int. Conf. on Wireless Algorithms, Aug. 1-3, 2007, pp. 219-224.

Jones, L, et al, "Wireless Physiological Sensor System for Ambulatory Use," <http://ieeexplore.ieee.org/xpl/freeabs_all.jsp?tp=&arnumber=1612917&isnumber=33861>, Apr. 3-5, 2006, 1 page.

Jovanov, Emil, et al, "A Wireless Body Area Network of Intelligent Motion Sensors for Computer Assisted Physical Rehabilitation," Journal of NeuroEngineering and Rehabilitation, Mar. 2005, 10 pages.

Kalpaxis, Alex, "Wireless Temporal-Spatial Human Mobility Analysis Using Real-Time Three Dimensional Acceleration Data," IEEE Intl. Multi-Conf. on Computing in Global IT (ICCGI'07), 2007, 7 pages.

(56) References Cited

OTHER PUBLICATIONS

Lee, Hyunseok, et al, A Dual Processor Solution for the MAC Layer of a Software Defined Radio Terminal, Advanced Computer Architecture Laboratory, University of Michigan, 25 pages.

Lee, Seon-Woo, et al., "Recognition of Walking Behaviors for Pedestrian Navigation," ATR Media Integration & Communications Research Laboratories, Kyoto, Japan, pp. 1152-1155.

Margaria, Rodolfo, "Biomechanics and Energetics of Muscular Exercise", Chapter 3, Oxford: Clarendon Press 1976, pp. 105-125.

Milenkovic, Milena, et al, "An Accelerometer-Based Physical Rehabilitation System," IEEE SouthEastern Symposium on System Theory, 2002, pp. 57-60.

Mizell, David, "Using Gravity to Estimate Accelerometer Orientation", Seventh IEEE International Symposium on Wearable Computers, 2003, 2 pages.

Ormoneit, D, et al, Learning and Tracking of Cyclic Human Motion: Proceedings of NIPS 2000, Neural Information Processing Systems, 2000, Denver, CO, pp. 894-900.

Otto, Chris, et al, "System Architecture of a Wireless Body Area Sensor Network for Ubiquitous Health Monitoring," Journal of Mobile Multimedia, vol. 1, No. 4, 2006, pp. 307-326.

Park, Chulsung, et al, "Eco: An Ultra-Compact Low-Power Wireless Sensor Node for Real-Time Motion Monitoring," IEEE Int. Symp. on Information Processing in Sensor Networks, 2005, pp. 398-403.

Ricoh, "Advanced digital technology changes creativity," <http://www.ricoh.com/r_dc/gx/gx200/features2.html>, Accessed May 12, 2011, 4 pages.

"Sensor Fusion," <www.u-dynamics.com>, accessed Aug. 29, 2008, 2 pages.

Shen, Chien-Lung, et al, "Wearable Band Using a Fabric-Based Sensor for Exercise ECG Monitoring," IEEE Int. Symp. on Wearable Computers, 2006, 2 pages.

Tapia, Emmanuel Munguia, et al, "Real-Time Recognition of Physical Activities and Their Intensities Using Wireless Accelerometers and a Heart Rate Monitor," IEEE Cont. on Wearable Computers, Oct. 2007, 4 pages.

Tech, Ang Wei, "Real-time Image Stabilizer," <http://www.mae.ntu.edu.sg/ABOUTMAE/DIVISIONS/RRC_Biorobotics/Pages/rtimage.aspx>, Mar. 23, 2009, 3 pages.

Wang, Shu, et al, "Location Based Services for Mobiles: Technologies and Standards, LG Electronics MobileComm," IEEE ICC 2008, Beijing, pp. 1-66 (part 1 of 3).

Wang, Shu, et al, "Location Based Services for Mobiles: Technologies and Standards, LG Electronics MobileComm," IEEE ICC 2008, Beijing, pp. 67-92 (part 2 of 3).

Wang, Shu, et al, "Location Based Services for Mobiles: Technologies and Standards, LG Electronics MobileComm," IEEE ICC 2008, Beijing, pp. 93-123 (part 3 of 3).

Weckesser, P, et al, "Multiple Sensorprocessing for High-Precision Navigation and Environmental Modeling with a Mobile Robot," IEEE, 1995, pp. 453-458.

Weinberg, Harvey, "MEMS Motion Sensors Boost Handset Reliability" Jun. 2006, <http://www.mwrf.com/Articles/Print.cfm?ArticleID=12740>, Feb. 21, 2007, 3 pages.

Weinberg, Harvey, "Minimizing Power Consumption of iMEMS® Accelerometers," Analog Devices, <http://www.analog.com/static/imported-files/application_notes/59351518533628845 99AN601.pdf>, 2002, 5 pages.

Wixted, Andrew J, et al, "Measurement of Energy Expenditure in Elite Athletes Using MEMS-Based Triaxial Accelerometers," IEEE Sensors Journal, vol. 7, No. 4, Apr. 2007, pp. 481-488.

Wu, Winston H, et al, "Context-Aware Sensing of Physiological Signals," IEEE Int. Conf. on Engineering for Medicine and Biology, Aug. 23-26, 2007, pp. 5271-5275.

Yoo, Chang-Sun, et al, "Low Cost GPS/INS Sensor Fusion System for UAV Navigation," IEEE, 2003, 9 pages.

Zypad WL 1100 Wearable Computer, http://www.eurotech.fi/products/manuals/Zypad%20WL%201100_sf.pdf, Jan. 16, 2008, 2 pgs.

\* cited by examiner

METHOD AND APPARATUS FOR A HEALTH PHONE

RELATED CASES

The present application claims the benefit of U.S. Provisional Application Ser. No. 60/795,398, filed Apr. 26, 2006.

FIELD OF THE INVENTION

The present invention relates to health data, and more particularly to a health phone to monitor user activity.

BACKGROUND

NTT DoCoMo, Inc. is marketing the F672i (Raku Raku Phone III) in Japan, the first mobile phone that also is a pedometer. The pedometer phone records your steps, and it also can e-mail them once a day to the address of the user's choice, or others can message the pedometer phone with a specific subject line to find out your pedometer data. Given the high rates of chronic conditions such as obesity, hypertension, diabetes and other conditions as well as broad cell phone adoption by teens in the US and Canada, adding a pedometer to cell phones will be a big public health benefit to encourage activity.

However, the NTT DoCoMo system provides very limited accountability, and no real-time data. Furthermore, there is no central data collection mechanism.

SUMMARY OF THE INVENTION

A method and apparatus providing a health phone utilizing a pedometer or accelerometer incorporated into a cellular telephone. The system is designed to receive activity data from the pedometer or accelerometer, and communicate the activity data to a remote server, the cellular telephone further designed to receive suggestions from the server, the suggestions generated based on the activity data received from the cellular telephone.

BRIEF DESCRIPTION OF THE DRAWINGS

The present invention is illustrated by way of example, and not by way of limitation, in the figures of the accompanying drawings and in which like reference numerals refer to similar elements and in which:

FIGS. 8A-F are exemplary screen shots.

DETAILED DESCRIPTION

Figure 1:
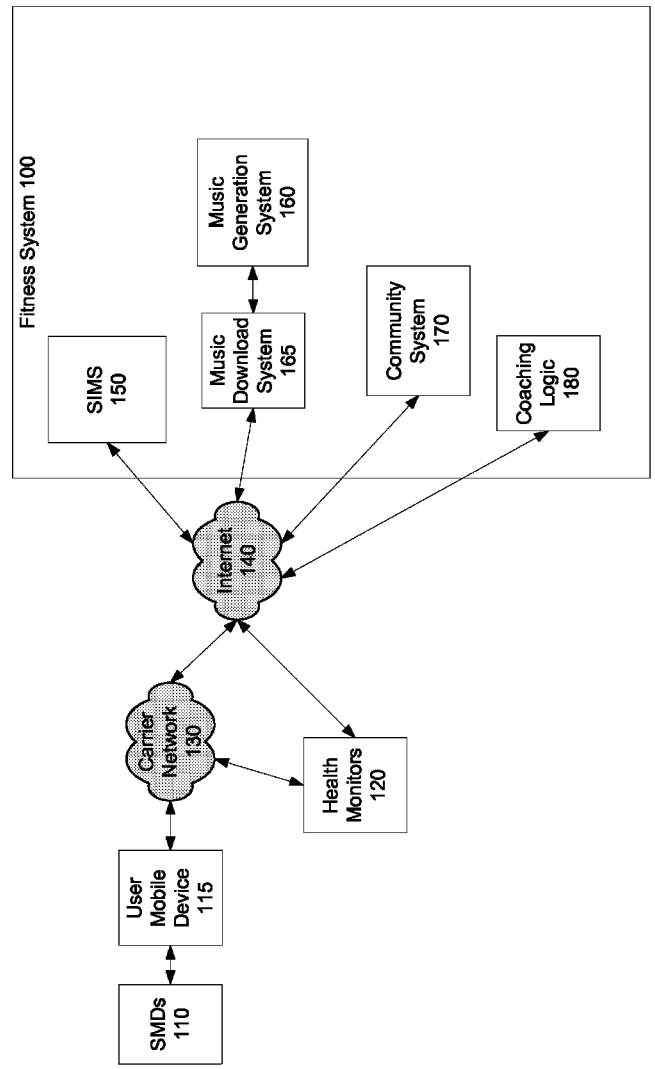
FIG. 1 is a block diagram of one embodiment of the network which may be used with the present invention.

The method and apparatus described uses a cellular telephone as a health phone. The health phone monitors user motion, activity and inactivity, and provides an unobtrusive and simple way of tracking key health information, such as activity level, heart rate, etc. In one embodiment, the system includes a feedback mechanism which provides the ability to remind a user after a period of inactivity to move. In one embodiment, the feedback mechanism may also suggest that a user do certain stretches or particular motions, in accordance with the user's health status. The health status includes health condition data and current activity data, as maintained on a server. In one embodiment, the activity monitoring is performed by a pedometer or accelerometer integrated into the user's mobile phone, creating a health phone.

In one embodiment, the system is a health phone with an integrated accelerometer. In one embodiment, the health phone may further include a receiver to communicate with a heart rate monitor, glucose monitor, and/or other health monitors. The heart rate monitor may be a chest strap type monitor, for example. The receiver may, in one embodiment, be a Bluetooth receiver, a wireless network receiver, a wired connection, or another type of receiving mechanism that enables the health phone to receive data from external sensors, monitors, and/or devices (SMDs). The health data, which may include the activity data and corresponding heart rate, is then sent to a central health data repository, which may reside on a remote server. The remote server may maintain cumulative data, and further provide analysis based on the data. In one embodiment, the remote server may also provide feedback to the user.

In one embodiment, the system includes an activity coach that reacts to the data from the health phone and reminds the user to maintain a certain level of activity throughout the day. In one embodiment, the activity coach also provides reminders based on the health data received through health monitors, whether coupled to the health phone or not. The user may have the option, in one embodiment, to select the message type, messaging mechanism, and messaging frequency.

One utility for the health phone—or more generally the health monitor/wireless communicator—is providing diabetes management. The data collected from the health monitor and cellular device is sent to a server. The server, in one embodiment, cross tabulates activity (measured by the activity/health monitor) versus blood glucose and insulin taken (or alternative health indicators) to have a more complete picture of what is going on with the diabetic user. It is useful for diabetics to see steps/activity level cross graphed with blood glucose levels. In one embodiment, the system can then make concrete recommendations. For example, a recommendation may be to walk another 2,000 aerobic steps to lower glucose levels to a better level. Walking a certain amount at a certain pace has a predictable effect on a person's blood glucose levels. There is some variation across different users, but the effects generally remain the same for a particular user from day to day. In one embodiment, the activity/glucose adjustment levels may be calibrated for the individual user, based on the data received from the system. As the user becomes more fit, these effects may change, but the change is gradual. In one embodiment the system utilizes the continuous data to update these correlations for the user. Similarly, a correlation may be found between blood pressure (for example from stress) and walking, resting heart rate and walking, etc.

In one embodiment, the activity monitor is a pedometer. The pedometer is a great way to measure the activity level of an everyday person. In one embodiment, in addition to being able to monitor steps via a pedometer, the accelerometer integrated into the health phone is also capable of detecting and monitoring other activities, such as bicycling, roller skating, etc. Cellular telephones are becoming more popular, and are one of the few devices that are carried constantly on the user's person, and thus are capable of providing health data such as steps (pedometer), heart rate (heart rate monitor), etc. Furthermore, by providing a community around the health data, the user receives support as well as a level of accountability unavailable with systems that do not include actual health monitor data.

In one embodiment, the system, in addition to collecting data, enables the creation of communities. Furthermore, the system is designed to encourage participation in the communities. While the user need not participate in order to receive the benefits of correlated health data and feedback, members in such communities generally encourage each other to do better. In one embodiment, the communities enable the user to compare their progress. In one embodiment, users can create peer competitions. The peer competition may be biased (i.e. handicapped like in golf), so that people of unequal health status can compete fairly. In one embodiment, each person gets an individualized "health score" based on the health data known about the person, and this health score is used to bias the competition. This enables an older fit person to fairly compete with a younger less fit person, a disabled person to compete with an able person, etc. In one embodiment, the system may create a handicapping based on the user health data in the server.

In one embodiment, in order to encourage walking, the system may enable setting up a virtual walk. A virtual walk enables users to track their walking goal, as the miles accumulate. For example, a goal may be to walk across America, or between any other start and destination. In one embodiment, the system may use third party mapping software to identify the length and steepness of the terrain, and prompt accordingly. In one embodiment, the system may further provide image-based feedback (for example showing representative images from a city or town virtually crossed by the user.

FIG. 1 is a block diagram of one embodiment of the network which may be used with the present invention. The user's mobile device 115 may be a cellular phone, a wearable computer, or any other device which is generally carried by the user and provides at least a periodic ability to establish a connection to the Internet 140. In one embodiment, the user's mobile device 115 connects to the Internet 140 via carrier network 130. At least one sensor, monitor, and/or device (SMD) 110, 120 is coupled to mobile device 115, or is part of the mobile device 115. Additional SMDs 110, 120 which may include various health monitors such as heart rate monitor, blood pressure monitor, blood glucose level monitor, pedometer, etc. send their data to the server 100 via user mobile device 115, or directly through carrier network 130 or Internet 140.

The health monitor and user device data is passed to server 100. Server 100, in one embodiment includes a fitness system 100. Fitness system 100 includes, in one embodiment SIMS 150, community system 170, and coaching logic 180. In one embodiment, each of the elements of the fitness system 100 may be on a separate server, or multiple servers. Alternatively, the elements may share a server or servers.

Figure 2:
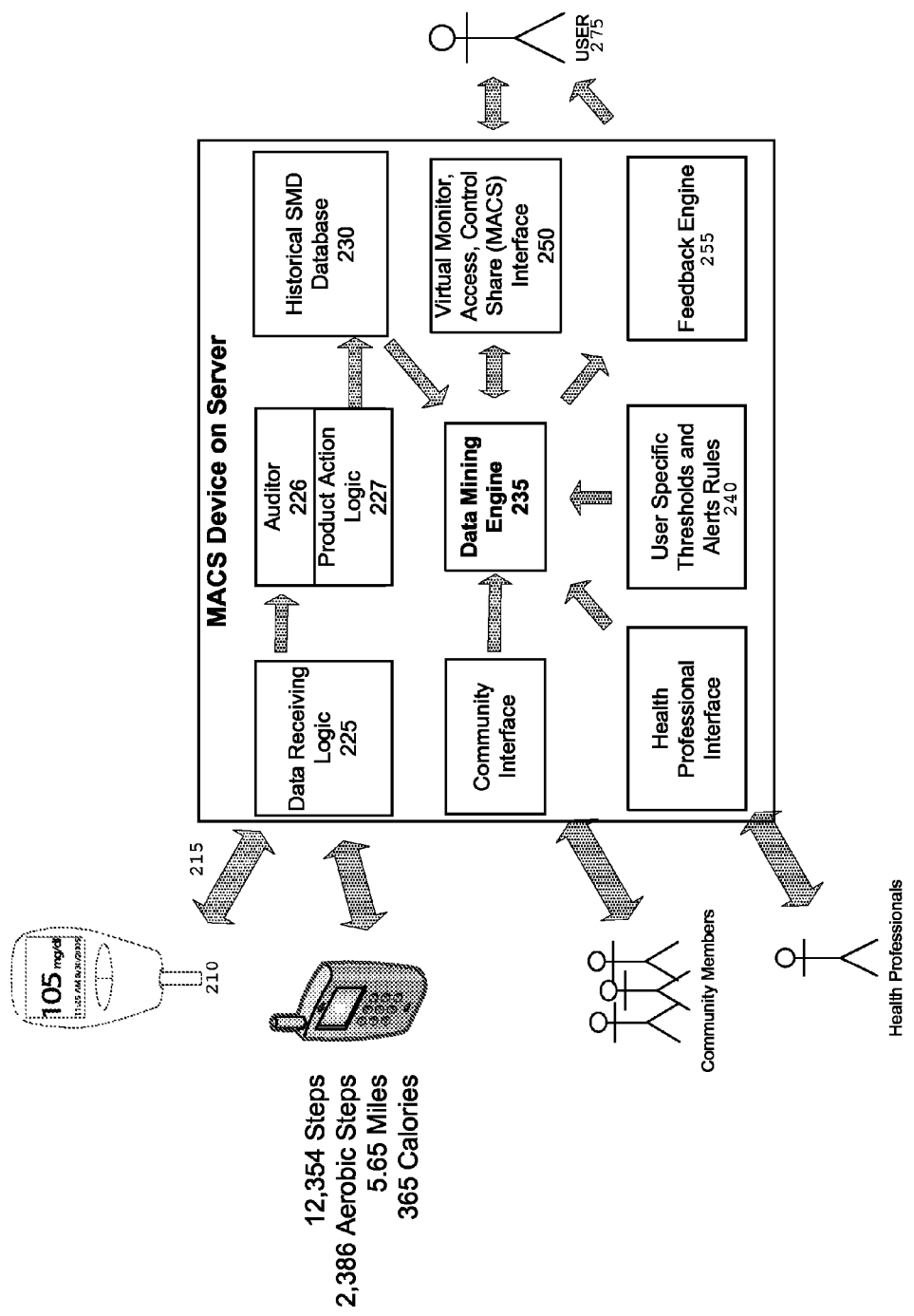
FIG. 2 is a block diagram of one embodiment of the MACS system.

FIG. 2 is a block diagram illustrating one embodiment of a Virtual Management, Access, Control, Share (MACS) device on the SIMS server and its relationship to the actual SMD. The actual SMD 210 has an intermittent connection 215 to a server 220. The connection 215 may be through the Internet, through a carrier network, or through other means. The server 220 may be located in the same location as the real SMD 210.

The data receiving logic 225 receives the data from the actual SMD 210 or the user via an intermittent connection 215. The data is stored in historical database 230. The historical data is used by data mining engine 235, to present virtual MACS device 250 via a reliable always-on connection 260 to various recipients 275. In a healthcare setting for example, the recipients may include the user, healthcare providers, and family.

In one embodiment, data mining engine 235 may further interface with user alerts and rules 240 to generate notifications through intelligent notification engine 255. Intelligent notification engine 255 can send automatic notifications to designated recipients 275, when certain threshold or alert conditions are met. The threshold or alert conditions may include historical data, trend analysis, variance from charted trends, simple threshold, or any combination of the use of historical and current data from the actual SMD 210, or combination of SMDs. In one embodiment, the data mining engine 235 constantly monitors the database 230, to ensure that the alert rules and user thresholds 240 have not been triggered. Intelligent notification engine 255 can, in one embodiment, trigger a notification in an appropriate format to any designated recipient.

In one embodiment, in addition to the database 230, data from other relevant actual SMDs may be received as well via logic 245. For example, in health setting, in addition to the glucose meter, exercise data, medical reports, and/or other relevant conditions may be monitored. The threshold and alert rules 240 may utilize a combination of data from more than one real SMD to trigger a notification or command 270.

Figure 3A:
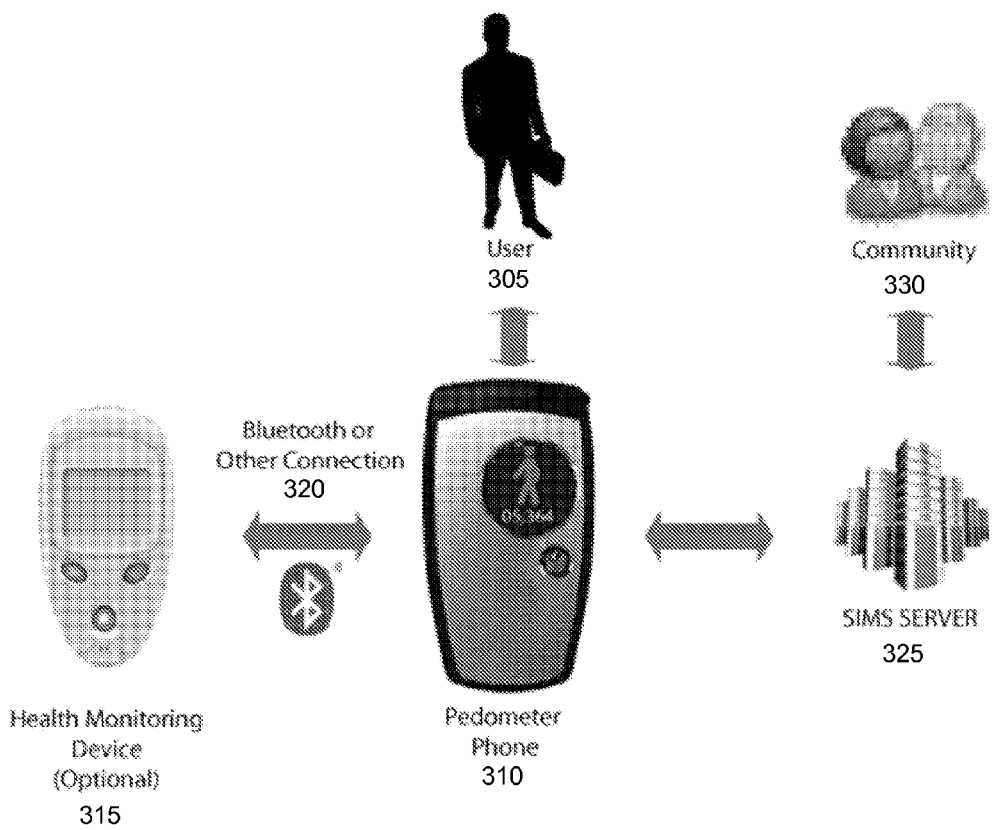
FIGS. 3A and 3B are exemplary sketches of the user system which may incorporate a health monitor and a mobile communications system.
Figure 3B:
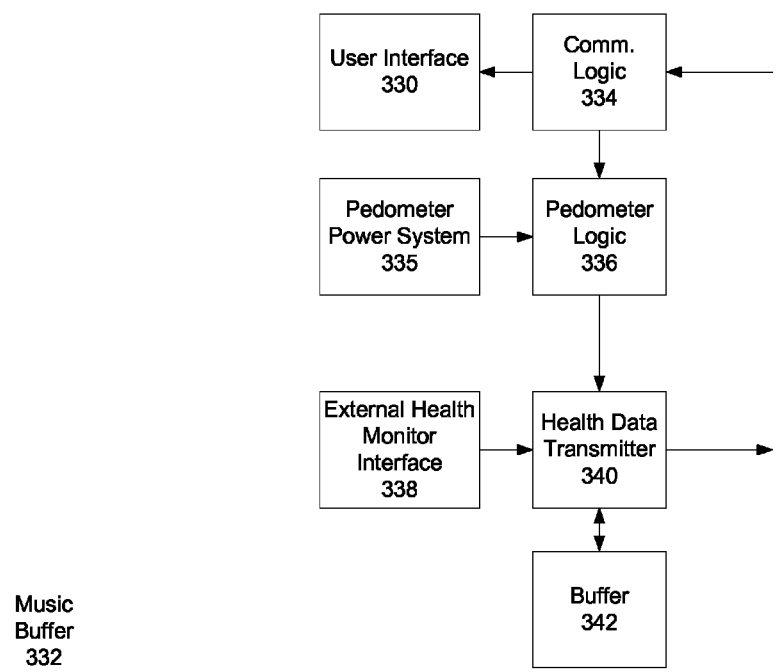

FIGS. 3A and 3B are exemplary sketches of the user system which may incorporate a health monitor and a mobile communications system.

FIG. 3A is a diagram of the client system elements. Health phone 310 includes mobile telephone functionality, a pedometer or other activity monitor, and the ability to send health data to a server. In one embodiment, additional health monitoring devices 315 may be coupled via Bluetooth or other connection 320 to health phone 310. Health phone 310 is carried by a user 305.

In one embodiment, the user's activity is tracked by an accelerometer in the health phone 310. In one embodiment, the accelerometer comprises a three-dimensional accelerometer. In one embodiment, the accelerometer comprises a two-dimensional accelerometer. In one embodiment, the accelerometer comprises two two-dimensional accelerometers arranged to enable detection of motion along all three axes. Alternative configurations for obtaining accelerometer data may be used.

The health phone 310 sends the activity data to SIMS server(s) 325. If additional health monitors 315 are coupled to health phone 310, the data from the health monitors 315 is also sent to the SIMS server(s) 325. In one embodiment, health phone 310 sends its data via cellular network or via the Internet if it is a WAP enabled phone. In one embodiment, SIMS server 325 shares parts of the data, or analyzed data, with community 330. Community 330 is designed to provide encouragement to the user 310, to maintain a fitness regimen. In one embodiment, user 305 accesses community 330 on the World Wide Web, via a browser, or via health phone 310. In one embodiment, the community 330 may also provide encouragement via email, instant messaging, or another format.

FIG. 3B is a block diagram of one embodiment of the client system. The client system includes an activity monitor 336. In one embodiment, the activity monitor 336 is a pedometer. In one embodiment, the activity monitor 336 is an accelerometer. The accelerometer may be a one, two, or three-dimensional accelerometer. In one embodiment, if the accelerometer is one or two-dimensional there may be two or more accelerometers that are part of the activity monitor 336. In one embodiment, the activity logic 336, which includes activity monitor 336 and temporary data storage for the activity monitor, is separately powered by activity monitor power system 335. The activity monitor power system 335 enables the activity monitor 336 to operate even when the client system (mobile telephone) is turned off.

The activity data from activity monitor logic 336 is transmitted to the server system via health data transmitter 340. In one embodiment, an external health monitor interface 338 is also included in the system. The external health monitor interface 338 is designed to receive health data from external health SMDs, such as glucose meters, heart rate monitors, etc. In one embodiment, external health monitor interface 338 is a Bluetooth interface, which is configured to receive health data from external health monitors. In another embodiment, external health monitor interface 338 may be a wired interface designed to receive a physically connected device. The data received via external health monitor interface is buffered, in one embodiment, and then passed on to health data transmitter 340.

In one embodiment, the health data is stored on the client system until health data transmitter 340 receives an acknowledgement that the data has been successfully received at the server (not shown). In one embodiment, a cyclic redundancy check (CRC) is included with the data, to ensure that the correct uncorrupted data was received by the server.

In one embodiment, the server may send feedback data to the health phone. The feedback data is received via communication logic 334. Communication logic 334, in one embodiment, passes feedback designed for the user to user interface 330. Feedback data, in one embodiment, may be text, audio data, or other types of data. In one embodiment, communication logic 334 may send some of the feedback data directly to activity monitor logic 336. For example, if the server determines that the accelerometer settings must be altered in some way, this data may be received from the server.

Figure 3C:
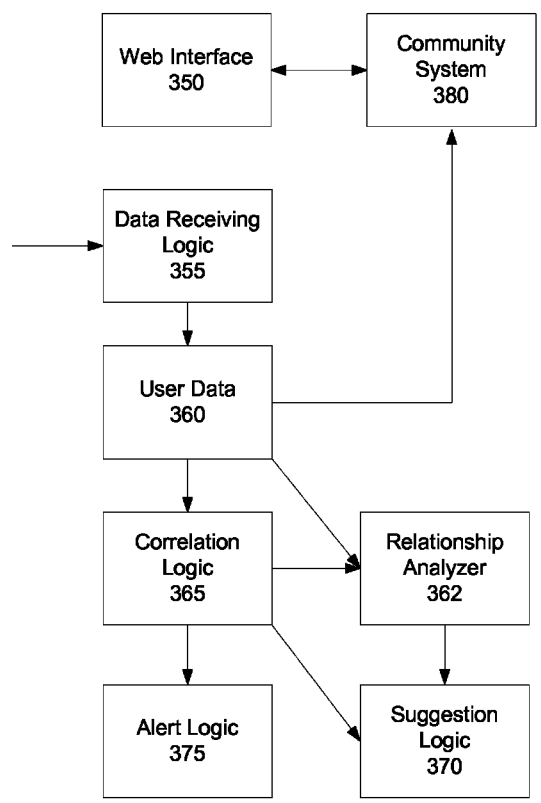
FIG. 3C is a block diagram of one embodiment of the server.

FIG. 3C is a block diagram of one embodiment of the server. The server receives data from the health phone via data receiving logic 355. Data receiving logic, in one embodiment, receives data from the health phone. In one embodiment, the data may include activity data as well as other available data. In one embodiment, the health data is pedometer data, which includes time & date information in addition to the step information.

The data received is then stored as user data 360. In one embodiment, user data is stored in a central database/repository. In one embodiment, this central database/repository includes security, so that user data is not directly accessible or modifiable.

Correlation logic 365 utilizes the data in user data store 360 to determine whether there needs to be an alert or suggestion made to the user. Alerts indicate that the user should do something right away. For example, if the health data includes glucose level data, and the trending analysis determines that the user's glucose levels will be causing a problem shortly, an alert may be sent, via alert logic 375. The alert may indicate an action to take, or an action to stop, in order to prevent a problem. In one embodiment, alerts may be in response to data, data trends, correlations between data sets, or pre-set alert levels. For example, a user may prefer to alert a third party if certain health indications happen.

Relationship analyzer 362 determines relationships between activity data (i.e. steps taken, speed of the steps, etc.) and other health data (i.e. blood glucose level, stress level, resting heart rate). The relationship analyzer 362 uses the correlation data and user data. In one embodiment, the relationships may be multi-level, with various factors obtained from various health monitors creating a complex relationship. In one embodiment, this relationship is user-specific. In one embodiment, the relationship analyzer 362 creates and stores an adjustment relationship.

Suggestion logic 370 is designed to utilize the correlation data from correlation logic 365 and propose actions to the user. For example, the suggestion logic 370 may suggest actions to the user based on the currently received data, historical/trend data analysis, and the user's other available data. In one embodiment, the suggestion may be a multi-step process. For example, the suggestion for a blood glucose level at a certain level may be to take 2000 aerobic steps now, and eat some high fiber, low glycemic index carbohydrates in one hour. In one embodiment, one of the suggestions is to walk, when the health phone includes a pedometer. In one embodiment, the suggestion logic 370 may send out an initial multi-step suggestion, and follow-up as the user follows or fails to follow the suggestion. In one embodiment, the initial suggestion may be a single step, with follow-up suggestions sent depending on whether the user followed the initial suggestion or not.

Figure 8A:
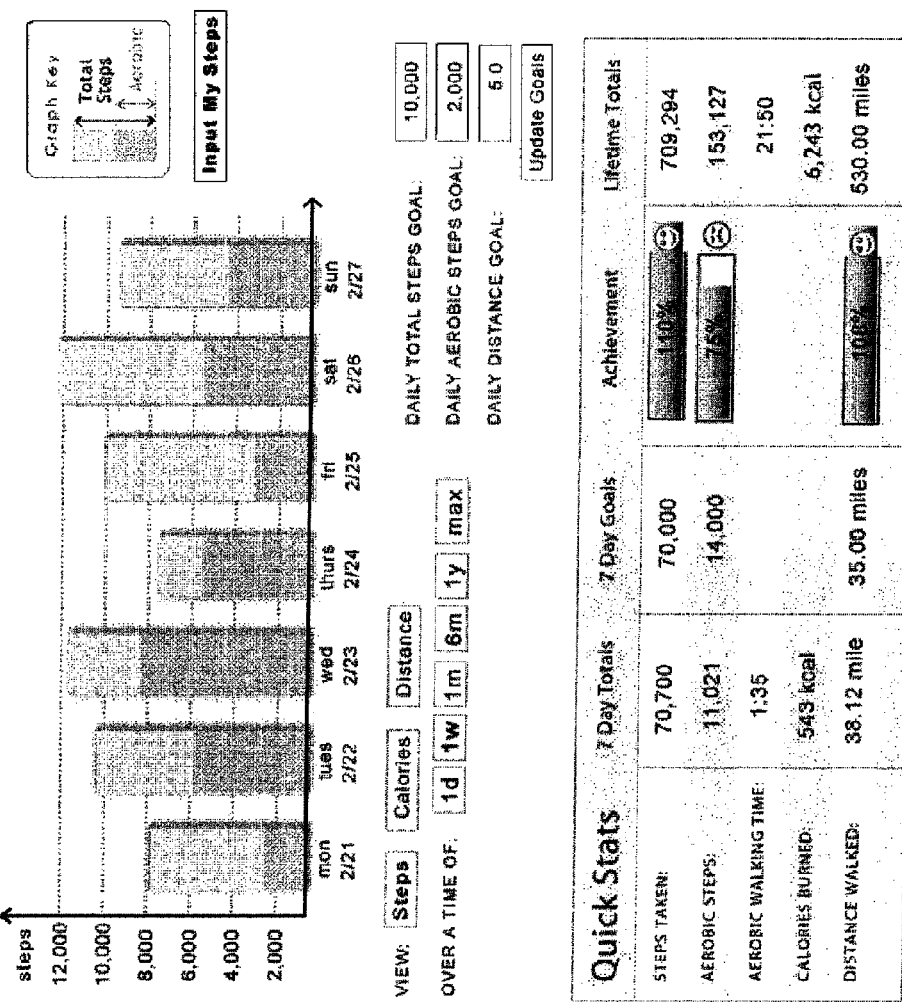
Figure 8B:
Figure 8C:
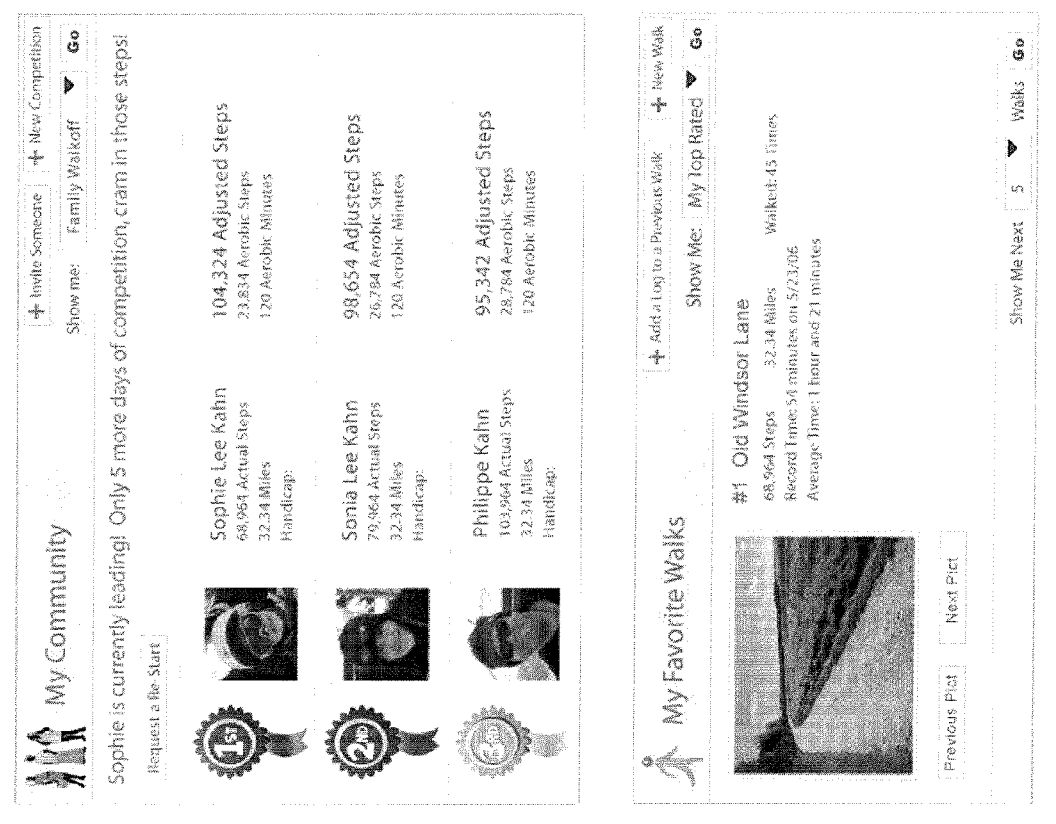
Figure 8D:
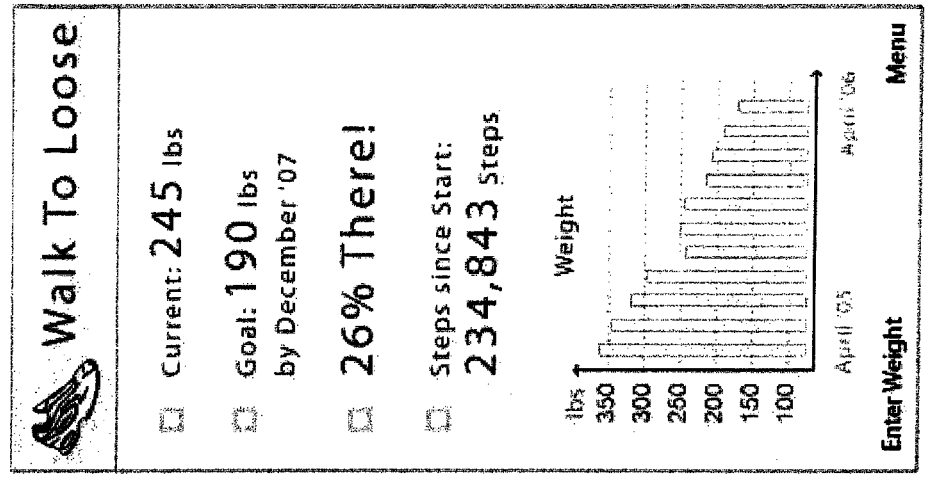
Figure 8D:
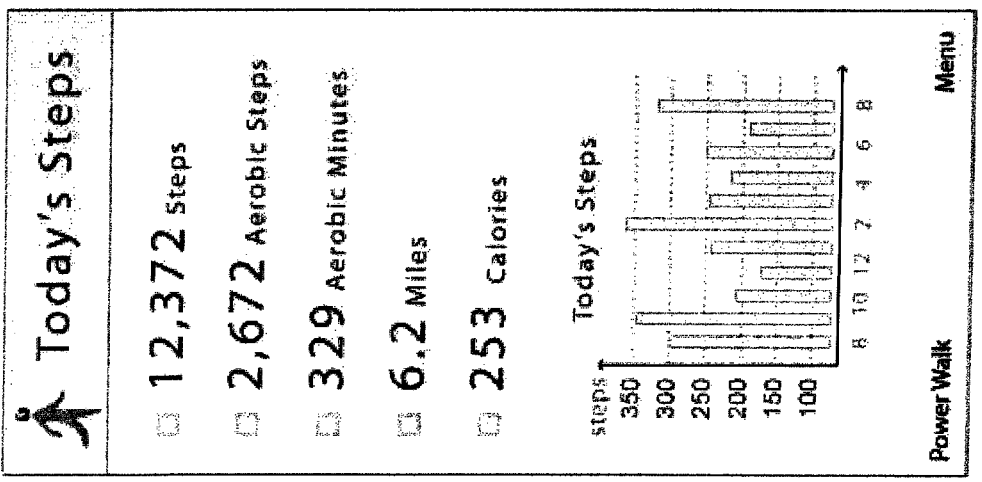

Web interface 350 enables the user, and other authorized viewers, to view user data 360, and adjust settings. In one embodiment, the web interface may be used to present the data to the user. FIG. 8A illustrates an exemplary screen shot showing the user's health data over time. FIG. 8D illustrates an exemplary display including the pedometer data collected, as well as goals and weight data. This type of data may be very motivational to users.

In one embodiment, the system also includes a community system 380. The community system 380 is designed to provide a community aspect to exercise and health monitoring. The community system 380 is described in more detail below, with respect to FIG. 6.

Figure 4:
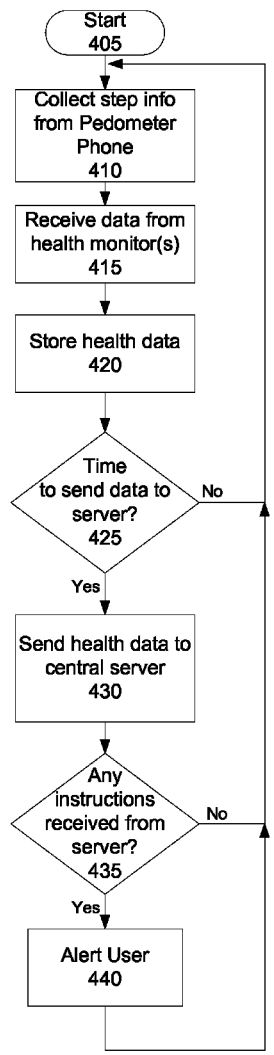
FIG. 4 is a flowchart of one embodiment of utilizing the health phone system including coaching.

FIG. 4 is a flowchart of one embodiment of the client-side process. This process is active whenever the user carries the health phone (block 410). The health phone may receive data from other external health monitors as well. These external health monitors may include any monitors that can communicate with health phone, that are used to assess the user's current health status. For example, the health monitors may include a blood glucose monitor, a heart rate monitor, a blood pressure monitor, a blood oxygen level monitor, or any other type of health monitor. These health monitors communicate their data to the health phone, in one embodiment. (block 415) In another embodiment, the health monitors may communicate their data directly to the server, without going through the health phone. In that case, block 415 may be skipped.

The health data is stored temporarily by the health phone (block 420). In one embodiment, the health phone simply stores data received from external health monitors, and whenever it sends its own pedometer data, it packages the external health monitor data along with it. In one embodiment, the health phone stores the pedometer/internal health data as well.

The process then determines whether it is time to send data to server (block 425). In one embodiment, the pedometer collects data continuously. In one embodiment, health monitors also may collect data continuously. The system, however, in one embodiment, only sends data periodically. In one embodiment, data is sent at preset intervals. In one embodiment, this interval may be one minute. In another embodiment, data may be sent only when at least a preset number of steps have been taken or a preset amount of health data has been collected, or a preset amount of time has elapsed, whichever occurs first. In another embodiment, the sending interval may be set based on another factor. If it is not yet time to send the data, the process returns to block 410 to continue collecting pedometer data. If it is time to send the data, the process continues to block 430.

In another embodiment, the data is stored in a buffer and immediately sent when received. In one embodiment, the pedometer data is stored separately by the pedometer aspect of the health phone, and only transmitted to the mobile-aspect of the health phone periodically. In one embodiment, in such a case the pedometer data is immediately forwarded when it is received by the mobile-aspect of the health phone.

The data is sent to the central server (block 430). In one embodiment, the data may be sent as an email, SMS, MMS, via WAP, or in another format. In one embodiment, the system awaits an acknowledgement that the data was correctly received by the server. In one embodiment, the data is erased from the health phone once the acknowledgement is received.

At block 435, the process determines whether any instructions or alerts have been received from the server. The server may return data to the user's health phone. The instructions/alerts may be received in response to the data sent, cumulative data from the user whether received through the health phone or other sources, or other occurrences. If no alerts are received, the process returns to block 410 to continue collecting data.

If an alert is received, the process informs the user (block 440). In one embodiment, the system uses the standard SMS/email alerting system which is part of the health phone. Thus, the system itself need not do anything to alert the user. In one embodiment, the data received may be an adjustment to the health device, or something else that need not trigger a user alert. In that case, in one embodiment, the system does not inform the user. In another embodiment, the user is informed of the update, but the information is passed without an alert.

The process then returns to block 410, to continue collecting data. Note that while this is described as a flowchart, these processes generally occur simultaneously. That is data is constantly collected, and whenever it is time, the data is sent. The system continuously monitors for data received from the server. The other flowcharts utilized in this application also need not be executed in a linear form.

Figure 5:
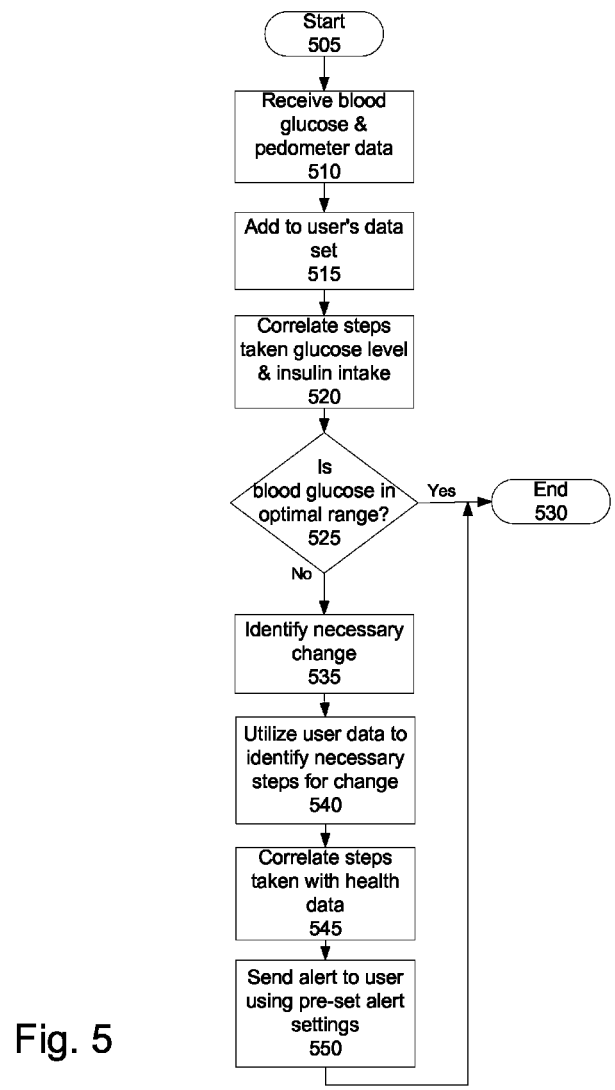
FIG. 5 is a flowchart of one embodiment of correlation evaluation and feedback.

FIG. 5 is a flowchart of one embodiment of correlation evaluation and feedback. Note that the example provided here correlates pedometer data (steps taken) with blood glucose data (blood sugar levels). However, this is merely an example, and the creation of correlation between two or more measurements would be understood by one of skill in the art. For example, heart rate over time may be correlated with blood oxygen levels or blood glucose levels. Blood pressure may be correlated to amount walked, etc. One of skill in the art would understand that there are other correlations which may be used.

At block 510, blood glucose and pedometer data is received. In one embodiment, the pedometer data is sent periodically by the health phone. In one embodiment, the blood glucose data is also received through the health phone. In another embodiment, the blood glucose data is received through a different path. In one embodiment, blood glucose data includes data from a blood glucose monitor as well as an insulin pump, or from a user indicating how much insulin was used.

The new data is added to the user's data set. As discussed in prior application U.S. Ser. No. 11/192,549, entitled "MONITOR, CONTROL, AND SHARE (MACS) SYSTEM," incorporated herein by reference, the system maintains a central data store. This central store enables the system to not only identify long-term trends, but also determine user history, and user-specific correlations. In one embodiment, additional data regarding any medicines or materials used to affect insulin levels may be included in the user's dataset. In one embodiment, the user's food data may also be included in this data set.

At block 520, the number of steps taken (i.e. pedometer data) is correlated with glucose levels. In one embodiment, other factors such as insulin taken, medicines taken, etc. are also included in the correlation. In one embodiment, the system continuously performs this correlation, as data is received. In one embodiment, the time of day is also taken into consideration for blood glucose levels. Generally, blood glucose levels are highest shortly after a meal. In one embodiment, meal data may be received from the user. In another embodiment, the system may determine when meals were consumed based on time-of-day data. In another embodiment, if the health phone has GPS (global positioning system) enabled, or if the pedometer data provides location information, the system may utilize this data to determine when the user eats.

At block 525, the process determines whether the glucose levels are in the optimal range. If the glucose levels are in the optimal range, the process terminates, at block 530. Otherwise, the process continues to block 535.

At block 535, the process identifies the necessary change in the glucose levels, to move them to optimal level. This may be to increase or decrease the blood glucose levels by a certain amount or percentage.

At block 540, the process uses user data to identify necessary steps for change. The user data collected indicates the correlation between changes in level of movement, level of insulin, food consumption, and other medicines and changes in blood glucose levels.

At block 545, the process determines the number of steps that should be taken, which would correlate with the necessary change. In one embodiment, the process takes into account a walking speed as well, in this evaluation. In one embodiment, for example, the system may know that walking 1000 aerobic steps reduces the user's blood glucose level by 2%. Therefore, the system may determine that the user should walk 2000 steps to reduce the blood glucose levels appropriately. Of course, while the pedometer-based recommendation is shown here, other recommendations—including eating something, taking medicines, performing other activities, may be recommended.

At block 550, the suggestion alert is sent to the user, indicating steps the user should take to appropriately alter the blood glucose levels. In one embodiment, the alert is sent using the mechanism selected by the user. In one embodiment, the suggestion alert is sent to the health phone. In one embodiment, the alert-type may be different depending on the level of deviation from the acceptable glucose levels. For example, if the level of deviation indicates that there may be a medical event, the alert may be sent to third parties as well. In one embodiment the notification process described in co-pending application Ser. No. 11/192,549 may be used. The process then ends at block 530.

Figure 6:
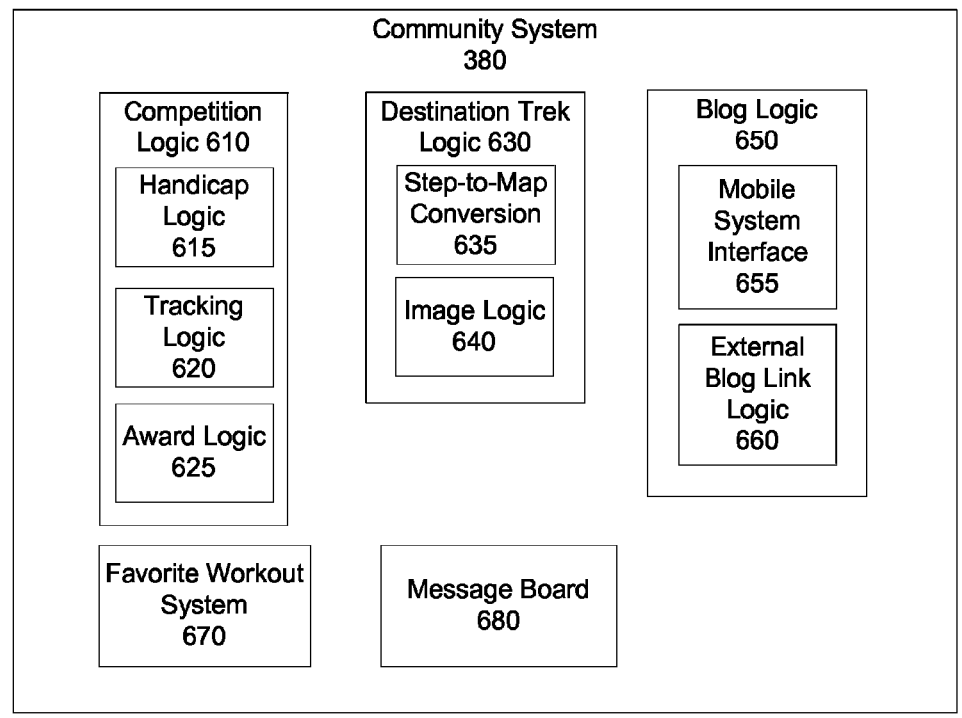
FIG. 6 is a block diagram of one embodiment of the community system.

FIG. 6 is a block diagram of one embodiment of the community system. The community system 380 is useful to encourage users to follow their exercise programs. There are multiple features.

Competition logic 610 administers competitions between users. Users can sign up for public competitions (i.e. visible to all users) or private competitions (i.e. visible only to those users who are invited to participate). Competitions administered by competition logic 610 may, in one embodiment, be handicapped. This enables unequal competitors to compete with each other. For example, if one of the competitors is a 10 year old, it would not be fair to compare step-for-step with a 24-year-old. Therefore, handicap logic 615 is used to generate a "fair" comparison. In one embodiment, handicap logic 615 takes into account the calculated fitness level of the user, based on the health data in the system about each user.

Competition logic 610, in one embodiment, calculates a "conversion to standard step" mechanism. Thus, for example, for a child, 1000 steps may be equivalent to 1200 "standard steps." Similarly, the level of exertion for "aerobic steps" may be different for an older person than for a younger person. FIG. 8F illustrates an exemplary display of a current competition. It shows the relative place of each participant in the Walk Off. FIG. 8C illustrates an exemplary display showing more information about the Walk Off, including current placement, how to catch up, etc.

Tracking logic 620 tracks how each user is doing in each competition. Award logic 625 shows the user's placements. This is shown in FIG. 8C. In one embodiment, the user's awards (i.e. final placements in various competitions) may be displayed publicly, if the user wishes. In one embodiment, current standings in on-going competitions may also be generated and displayed, in accordance with the user's preference. In one embodiment, award logic 625 may display standings in public competitions in the blogging system 650, next to entries on the message board 680, and in other places. In one embodiment, lower placements may be replaced by a "participant" icon. This again provides positive feedback to the user, and incentives to excel. In one embodiment, competitions may focus on "steps taken" for pedometer-type devices, length and frequency of workouts, vigorousness of workout, or other metrics.

Figure 8E:
Figure 8F:
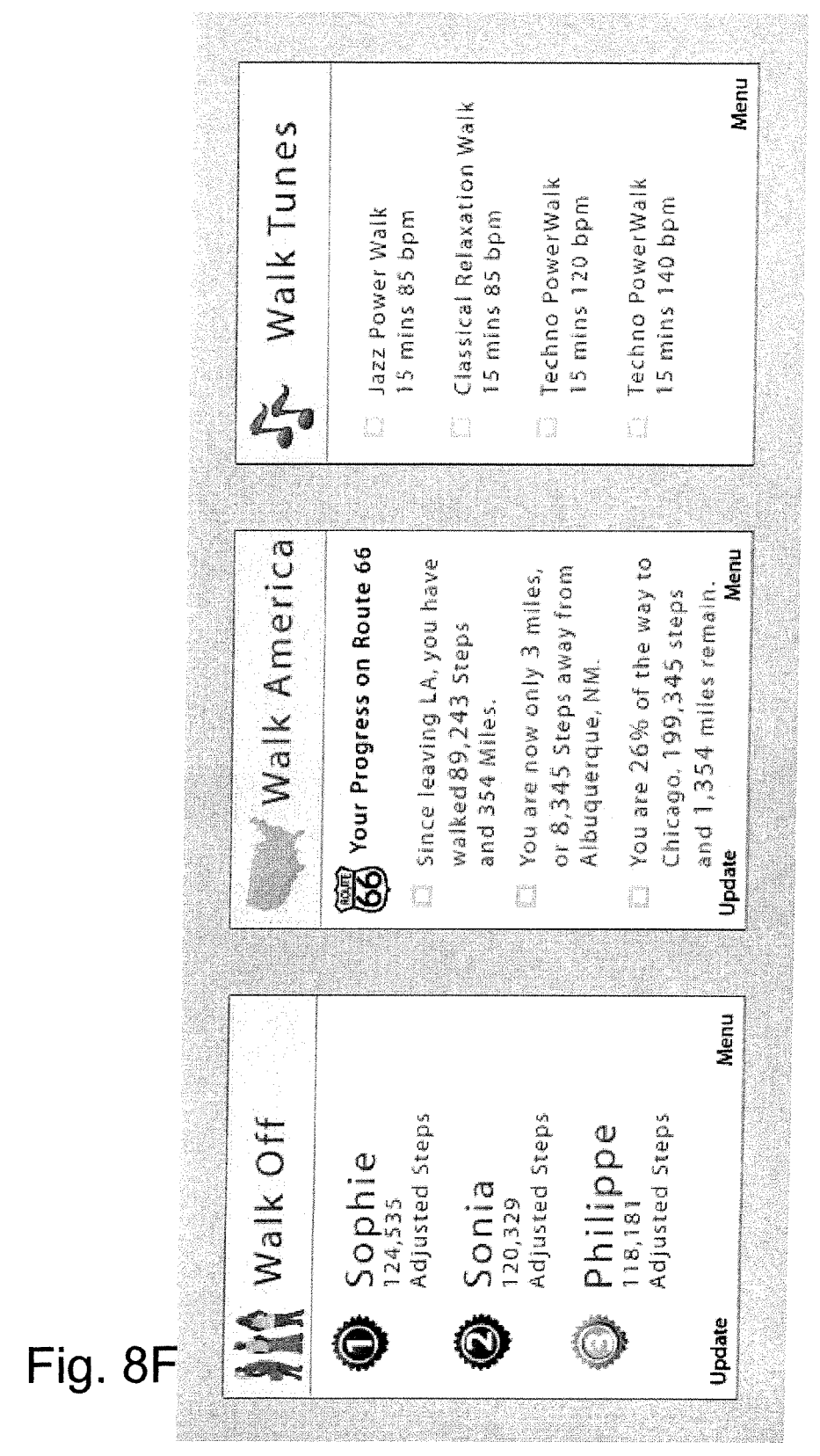

Destination trek logic 630 enables the system to provide competitions for taking a particular trek. For example, users may decide to walk across America, climb the Rockies, walk to their home town, or select an alternative "destination" or series of destinations. In one embodiment, the starting and ending points for the trek may be arbitrarily defined by the user. Step-to-map conversion logic 635 takes the source and destination, and step size data from the user. This is used to calculate how far the user travels, using the pedometer data. FIG. 8E is an exemplary display of the trek Walk America, and the user's progress on that trek.

In one embodiment, the health phone data is used to chart progress. In one embodiment, self-reporting may be used, and the user may enter, for example, miles from a treadmill. Image logic 640 enables the destination trek logic 630 to insert images from actual location which is being virtually walked. Thus, for example, the user may set as a target walking from the Golden Gate Bridge to Coit Tower. The system may provide images along that walk for further motivation. In one embodiment, the system may also provide feedback/motivation based on the virtual locations. For example, in the Golden Gate Bridge to Coit Tower trek, the feedback may encourage the user to continue walking with messages such as "You are already at Fort Mason, that's more than half-way there!" etc.

Blog logic 650 enables the user to keep a personal web log. An exemplary web blog display is shown in FIG. 8B. In one embodiment, an existing blogging engine may be used. In one embodiment, the user may be permitted to post from a mobile device, using mobile system interface 655. In one embodiment, the blog logic 650 may automatically post blog posts for various fitness sessions. For example, the blog logic 650 may automatically generate an entry for each workout session. In one embodiment, the entry may describe the user's workout. Again, this provides positive feedback to the user, and may encourage the formation of communities. In one embodiment, external blog link logic 660 enables the user to transmit blog entries in blog logic 650 to another blogging platform.

Favorite workout system 670 enables users to describe their favorite workouts, including fitness routines, walking paths, and other types of workouts. An exemplary favorite workout is shown in FIG. 8C. Again, this is designed to encourage community, and to encourage other users to try someone else's favorite workout. In one embodiment, the system may display these favorite workouts to users looking for new routines. In one embodiment, the system may further provide location-based filtering. For example, for a user known to be residing in Northern California, only local walks would be shown. In one embodiment, the user may further add "places I visit" or similar indications to see favorite walks elsewhere. In one embodiment, the system may receive location information from the user's mobile device, and use this information to tailor the "local walks" in the favorite workout system 670. This may enable a visitor to an area to find a nice workout.

Message board 680 enables users to communicate in other ways. Communities are designed to encourage people to meet.

In one embodiment, message board communities may be formed by the system. For example, there may be a message board for each identified type of medical status. For example, a board may focus on people having a particular type of condition, such as Type 2 Diabetes. In one embodiment, as the system acquires data about the user's condition and health status, it recommends message boards 680 which may be useful to the user. In one embodiment, as communities are formed on the message boards, competition logic 610 recommends friendly competitions between the members of the message boards.

Figure 7:
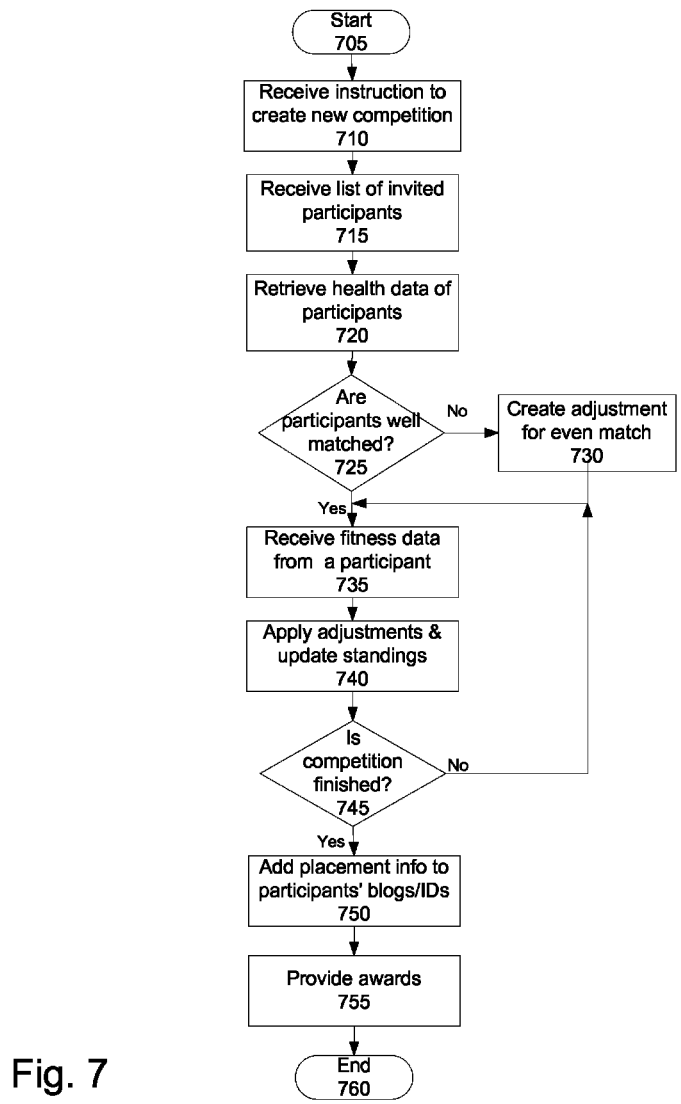
FIG. 7 is a flowchart of one embodiment of setting up competitions based on the health parameter data, to encourage a health regimen.

FIG. 7 is a flowchart of one embodiment of setting up competitions based on the health parameter data, to encourage a health regimen. At block 710, the system receives an instruction to create a new competition. In one embodiment, a new competition is created by a user. In one embodiment, the user may name the competition arbitrarily. At block 715, a list of participants is received. In one embodiment, the list of participants may be entered by the user. In another embodiment, the user may simply designate that the competition is open to the public. If the participant list is open to the public, in one embodiment, as each user signs up, the below steps are performed. If the list of participants is provided, the below steps may be performed immediately, or when an invited participant indicates an intention to join the competition.

At block 720, the health data of the participants—i.e. those who have indicated an intention to participate—is retrieved. In one embodiment, this is done as each participant joins. In another embodiment, this is done for all participants at the same time, when the competition actually starts. In another embodiment, this is done for all participants at the same time, when all invited participants have indicated their intention to participate, or not participate, in the competition.

At block 725, the process determines whether the participants are well matched. If so, the process continues to block 735. Otherwise, at block 730, an adjustment is created. This is referred to as handicapping. At its most basic, the adjustment may be for age and height. More complexly, the adjustment may include age, fitness level, past participation and success rate in competitions, health conditions, and any other relevant information. The adjustment is designed to ensure that each participant has an equal opportunity to win the competition. In another embodiment, this step may be skipped. In one embodiment, the user organizing the competition may select whether handicapping should be included.

Once the competition starts, the process described in blocks 735 through 755 is performed. Fitness data is received—continuously or on a periodic basis—from each of the participants, at block 735. In one embodiment, pedometer data is received as described above. At block 740, any handicap adjustments are applied to the fitness data, and the standings in the competition are updated. In one embodiment, the standings are always visible to the participants.

At block 745, the process determines whether the competition is finished. If the competition is not yet finished, the process returns to block 735, to continue receiving data from the participants.

If the competition is finished, the process continues to block 750. At block 750, placement information is added to the user's data. In one embodiment, the user's top 3 placements may be displayed along with his or her name/ID on message boards, blogs, and other interactions. This is designed to provide additional incentive for participation. In one embodiment, the placement information is displayed during the competition as well, to encourage people to use the network and the system. In one embodiment, any user can click update and get the latest data from all participants and see the latest results.

In one embodiment, at block 755, awards are provided. In one embodiment, the user organizing the competition may designate awards—whether connected to the system or not. In one embodiment, for system-created competitions (i.e. all people with Type 2 diabetes, or members of a particular message board) the system may provide awards which may range from free service, additional feature availability, to cash awards or other prizes. The process then ends at block 760.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative rather than a restrictive sense.

What is claimed is:

1. A mobile device comprising:
an activity monitor integrated into the mobile device to generate activity data;
a receiver to receive health data from one or more external health monitors;
a processor to execute computer-readable instructions to control a data transmitter to communicate the health data and the activity data to a remote server;
the processor implementing a communication logic to receive an initial suggestion from the remote server;
the data transmitter to transmit to the remote server subsequent health data and subsequent activity data to enable the remote server to determine whether the user followed the initial suggestion; and
the communication logic to receive a follow-up suggestion, the follow-up suggestion generated by the remote server based on a correlation between changes in health data received over time from the data transmitter and activity data received over time from the data transmitter; and
a blog logic to automatically generate a blog post based on the activity data, and the blog logic to further post the blog post for user.

2. The mobile device of claim 1, further comprising:
an external health monitor interface to receive the health data from the one or more external health monitors for transmission to the remote server by the data transmitter.

3. The mobile device of claim 2, wherein the one or more external health monitors are selected from among the following: a heart rate monitor, a blood pressure monitor, a blood glucose level monitor, an insulin pump, a pedometer, and a blood oxygen monitor.

4. The mobile device of claim 1, further comprising:
a user interface to notify the user of the initial suggestions generated by the remote server and of the follow-up suggestion generated by the remote server.

5. The mobile device of claim 1, further comprising:
the communication logic to further receive feedback for an exercise session of the user based on data associated with the exercise session and a virtual destination selected by the user, the feedback for the exercise session comprises one or more of a message encouraging the user, a message providing motivation based on the virtual destination selected by the user, and an image of a second location along a path to the virtual destination selected by the user.

6. The mobile device of claim 1, further comprising;
an activity monitor power system to separately power the activity monitor, to enable the activity monitor to continue monitoring user activity when the mobile device is turned off; and
a temporary storage to store activity data when the mobile device is turned off.

7. A computer-implemented health server comprising:
an interface to receive health data from one or more health monitors, the health data comprising one or more of: insulin data, food data, and glucose data, and activity data from a remote mobile device;
a processor implementing a correlation logic designed to determine a correlation between the health data and the activity data from the remote mobile device;
a coaching logic to send coaching data to a user, the coaching data providing an initial suggestion to the user for an exercise session based on the correlation between the health data and the activity data;
the coaching logic to determine whether the user is following the initial suggestion based on subsequent health data and/or subsequent activity data received by the interface, and to send a follow-up suggestion to the user based on a correlation between changes in health data received over time by the interface and activity data received over time by the interface; and
a blog logic to automatically generate a blog post for the exercise session of the user, the blog post describing the exercise session, and the blog logic to further to post the blog post for the exercise session to a social media site.

8. The health server of claim 7, further comprising:
a relationship analyzer to identify a relationship between the activity data and a change in a health condition.

9. The health server of claim 7, further comprising:
a community system to provide a community to encourage healthy user behavior, the community comprising a plurality of users associated with a plurality of computing devices, wherein the plurality of computing devices are accessible to the health server;
a communication interface to provide information associated with the user to the community system using a communication network; and
a memory to store the information associated with the user.

10. The health server of claim 9, further comprising:
a competition logic to enable users to set up competitions between users for a number of steps taken, as measured by a pedometer.

11. The health server of claim 9, further comprising:
a handicapping logic to provide a relative-ability based adjustment to the steps taken measurements, for competitions, enabling unequal users to participate in competitions.

12. The health server of claim 9, further comprising:
a favorite workout system enabling users to upload their favorite walks, and enabling other users to follow the favorite walks.

13. The health server of claim 12, wherein the favorite workout system filters the favorite walks provided to the other users based on a location of the other users.

14. A computer-implemented health server comprising:
an interface to receive data from one or more health monitors and one or more activity monitors, wherein health monitor data received from the one or more health monitors comprises one or more of: insulin data, food data, and glucose data;
an integration system using a processor designed to combine the health monitor data with activity monitor data received from the one or more activity monitors, to cross-tabulate the activity monitor data and the health monitor data, to determine a correlation between the cross-tabulated data, to provide a complete health picture to a user;
a suggestion logic to send an initial suggestion based on cross-tabulated activity monitor data and health monitor data to the user for how to improve the current health picture, to determine whether the user is following the initial suggestion based on subsequent health monitor data and/or activity monitor data received by the interface and to send a follow-up suggestion to the user, the follow-up suggestion based on a correlation between changes in the health monitor data received over time by the interface and activity monitor data received over time by the interface; and
a favorite workout system enabling users to upload their favorite walks to enable other users to follow the favorite walks, wherein the favorite workout system filters the favorite walks provided to the other users based on a location of the other users.

15. The health server of claim 14, further comprising:
a relationship analyzer to identify a relationship between the activity data and a change in a health condition based on the health data.

16. The health server of claim 14, further comprising:
a community system to provide a community to encourage healthy user behavior, the community comprising a plurality of users associated with a plurality of computing devices, wherein the plurality of computing devices are accessible to the health server;
a communication interface to provide information associated with the user to the community system using a communication network; and
a memory to store the information associated with the user.

17. The health server of claim 14, further comprising:
a competition logic to enable users to set up competitions between users for a number of steps taken, as measured by a pedometer.

18. The health server of claim 17, further comprising:
a handicapping logic to provide a relative-ability based adjustment to the steps taken measurements, for competitions, enabling unequal users to participate in competitions.

19. A computer executable method implemented by a health server comprising a processor, the computer-executable method comprising:
receiving health data from one or more health monitors and activity data from an activity monitor integrated into a mobile device via a network, the health data comprising insulin data, food data, and glucose data;
sending coaching data to a user through the network, the coaching data providing an initial suggestion to the user;
determining, by the processor, whether the user is following the initial suggestion based on subsequent health data and subsequent activity data and to send a follow-up suggestion to the user, wherein the follow-up suggestion is based on a correlation between changes in health data received over time and activity data received over time; and
providing feedback for an exercise session of the user based on data associated with the exercise session and a virtual destination selected by the user; and
providing a social media system to post about a user's workout session, the user's system including a blog logic to automatically generate blog posts for the exercise sessions of the user, each blog post describing the exercise session, and the blog logic to further to post the blog post to the social media system.

20. A computer-executable method implemented by a mobile device comprising a processor and memory, the computer-executable method comprising:
receiving data from one or more health monitors and one or more activity monitors integrated into the mobile device, the health monitor data comprising one or more of: insulin data, food data, and glucose data;
separately powering the integrated activity monitor, to enable the activity monitor to continue monitoring user activity when the mobile device is turned off;
combining, by the processor, the health monitor data with the activity monitor data;
cross-tabulating, by the processor, the activity monitor data and the health monitor data;
determining, by the processor, a correlation between the cross-tabulated activity monitor data and health monitor data to provide a complete health picture to a user;
sending, by the processor, an initial suggestion based on the cross-tabulated data to the user for how to improve the current health picture, when the initial suggestion is walking, including a recommended walk based on a favorite walk uploaded by another user, filtered based on the user's location;
determining, by the processor, whether the user is following the initial suggestion based on subsequent health data and/or subsequent activity data and sending a follow-up suggestion to the user, the follow-up suggestion based on a correlation between changes in health monitor data received over time and activity monitor data received over time.

* * * * *